US006688255B2

(12) United States Patent
Donaldson et al.

(10) Patent No.: US 6,688,255 B2
(45) Date of Patent: Feb. 10, 2004

(54) ROBOTIC APPARATUS AND METHODS FOR MAINTAINING STOCKS OF SMALL ORGANISMS

(75) Inventors: Jeffrey D. Donaldson, Tigard, OR (US); William W. Fisher, Berkeley, CA (US); Douglas O. Keller, Lake Oswego, OR (US); Troy M. Swartwood, Seattle, WA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 10/120,117

(22) Filed: Apr. 9, 2002

(65) Prior Publication Data

US 2003/0188698 A1 Oct. 9, 2003

(51) Int. Cl.[7] ............................................. A01K 29/00
(52) U.S. Cl. ....................................... 119/6.5; 119/678
(58) Field of Search ......................... 119/6.5, 678, 420, 119/417, 418, 843, 840, 842, 844, 712, 128

(56) References Cited

U.S. PATENT DOCUMENTS

| 3,228,061 | A | * | 1/1966 | Hughes ................ 128/202.13 |
| 4,224,898 | A |   | 9/1980 | Flagg et al. |
| 4,348,985 | A | * | 9/1982 | Leong .................... 119/420 |
| 4,759,228 | A | * | 7/1988 | Butler et al. .................. 73/866 |
| 4,941,431 | A | * | 7/1990 | Anderson, deceased et al. ........................ 119/420 |
| 5,297,502 | A | * | 3/1994 | Jaeger .................... 119/420 |
| 5,699,755 | A | * | 12/1997 | Wills et al. ................. 119/846 |
| 5,981,565 | A | * | 11/1999 | Wu ........................... 514/404 |
| 6,092,487 | A | * | 7/2000 | Niki et al. .................... 119/420 |
| 6,352,076 | B1 | * | 3/2002 | French ................. 128/203.12 |
| 6,477,987 | B2 | * | 11/2002 | Taylor ......................... 119/843 |

OTHER PUBLICATIONS

Bols. L, Bongarts et al., "Dual Color Fluorescence Sorting," *COPAS Application Note B–06*, Rev. A (date unknown).
Dell'Orfano, B.W., "Rapid Drosophila Embryo Sorting," *COPAS Application Note S–01*, Rev. D, (date unknown).

* cited by examiner

*Primary Examiner*—Yvonne Abbott
(74) *Attorney, Agent, or Firm*—Klarquist Sparkman LLP

(57) ABSTRACT

According to one embodiment, a robotic apparatus for maintaining a collection of stocks of small organisms, such as fruit flies, is capable of performing various tasks, including automatically transferring live flies from a donor container to a recipient container, such as for the purpose of feeding the flies. The apparatus includes an anesthetizing mechanism configured to automatically introduce an anesthetic, such as gaseous $CO_2$, into a donor container of live flies to temporarily immobilize the flies before the flies are transferred to the recipient container. The apparatus also includes a gas manifold that is configured to direct a flow of gas from a compressed-gas source into the donor container such that the immobilized flies are blown from the donor container into the recipient container. In another embodiment, automated methods are provided for maintaining a collection of stocks of small organisms, such as fruit flies.

51 Claims, 16 Drawing Sheets

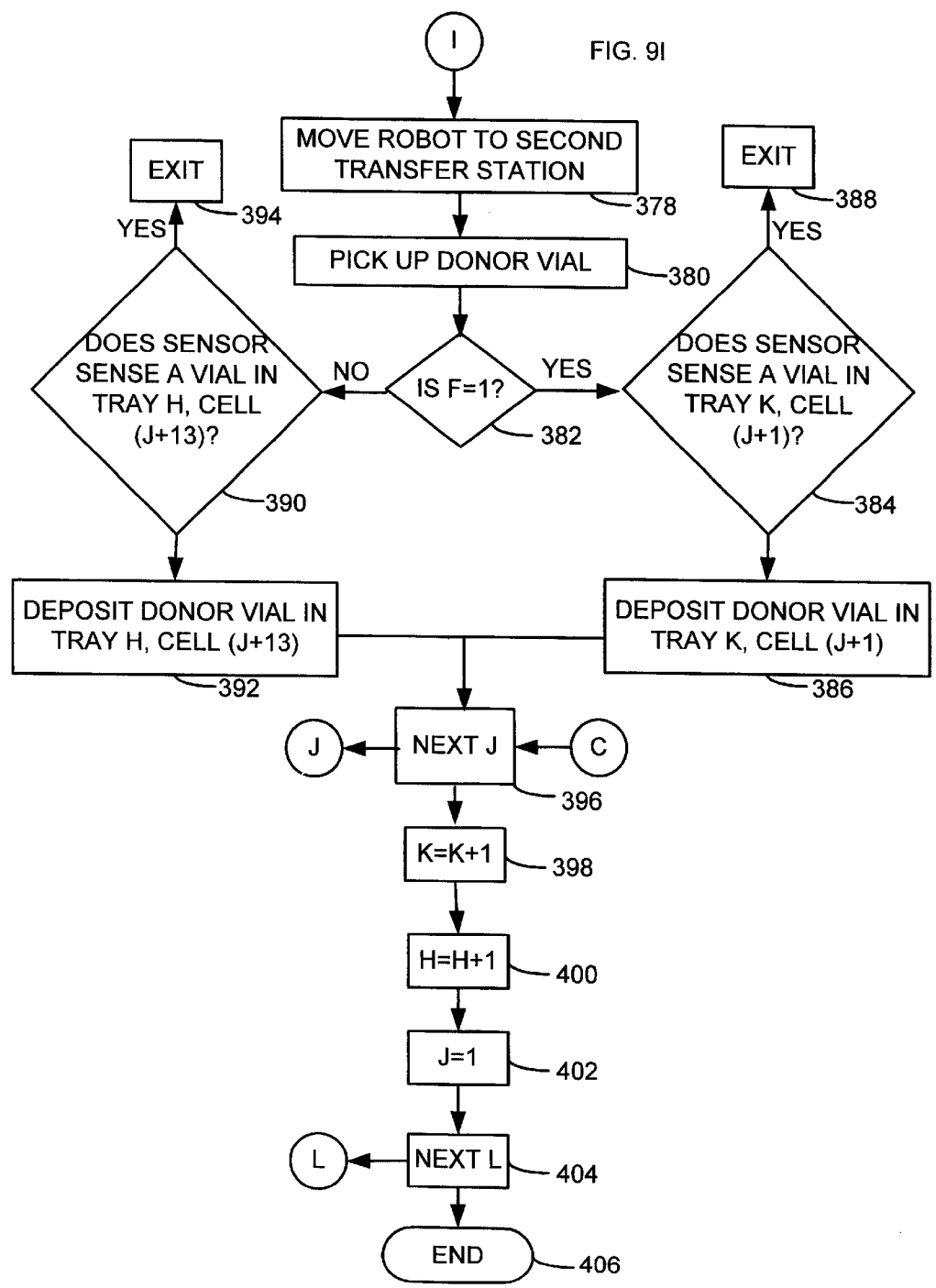

ns, useful in
ROBOTIC APPARATUS AND METHODS FOR MAINTAINING STOCKS OF SMALL ORGANISMS

FIELD

The present invention concerns robotic apparatus and methods for maintaining stocks of small organisms, such as fruit flies or any of various other small organisms, useful in the study of genetics.

BACKGROUND

*Drosophila melanogaster*, also known as the common fruit fly, is particularly useful in biological research, such as in genetics and developmental biology, because it is a small animal, has a short life cycle, and is easy to keep in large numbers.

The life cycle of the fruit fly has four stages: (1) the egg stage; (2) the larval stage; (3) the pupal stage; and (4) the adult stage. During the egg stage, an egg develops and hatches into a worm-like larva. During the larval stage, the larva eats and grows continuously over the course of several days. The larva then transforms into a pupa, which matures into an adult fly over the course of several days.

Research institutions and commercial entities maintain stocks of flies for their own use and/or for selling to other researchers. A collection of stocks may includes hundreds, sometimes thousands, of vials or containers, each containing a population of flies belonging to a particular genotype.

To sustain a population of adult flies, the flies must be periodically transferred to a new vial containing a fresh supply of food. Typically, flies kept at about 18° C. must be supplied with fresh food about every 8 weeks, although the exact time interval may vary depending upon the conditions in which the flies are kept. Generally, supplying the flies with fresh food involves placing a vial of flies, in an upside down position, on top of a vial of fresh food, with the open tops of the vials held tightly against each other to prevent the flies from escaping. Then, by tapping the vials against the top of a table, the flies are caused to fall from the upper vial into the lower vial. It is readily appreciated that feeding an entire collection of stocks requires a large number of monotonous man-hours. This process of manually transferring fly populations to vials of food may even cause repetitive-motion injury to personnel maintaining the stocks.

Hence, there is a need for automated equipment capable of maintaining a collection of flies.

SUMMARY

The present invention concerns an apparatus useful in maintaining a collection of small organisms, such as insects. The apparatus performs various tasks, one of which is the automatic transfer of live organisms (e.g., fruit flies) from donor vials, or containers, to corresponding recipient vials, or containers, such as for the purpose of feeding the organisms. In addition, in an illustrated embodiment, the apparatus makes bar-code labels for applying to recipient vials and is capable of reading bar-code labels on donor and recipient vials.

According to one representative embodiment, an apparatus is provided for transferring live organisms from a donor container to a recipient container. The apparatus comprises a source of an anesthetic, such as $CO_2$, for temporarily immobilizing the organisms in the donor container and a source of compressed gas for blowing the immobilized organisms from the donor container into the recipient container.

In particular embodiments, a transfer device is configured to automatically introduce the anesthetic into the donor container for temporarily immobilizing the organisms. An illustrated transfer device comprises a needle fluidly connectable to the source of the anesthetic. The transfer device is operable to insert the needle into the donor container (e.g., through a porous plug in the donor container) for injecting the anesthetic into the donor container.

The illustrated transfer device also includes a gas manifold that is adapted to receive the open tops of the donor and recipient containers and is fluidly connectable to the source of compressed gas. The gas manifold is configured to direct the flow of gas into the donor container such that the organisms are carried by the flow of gas into the recipient container.

The compressed-gas manifold in disclosed embodiments comprises a manifold block defining an opening extending through the block. The opening is dimensioned to receive the open top portion of a donor container on one side of the block and the open top portion of the recipient container on the other side of the block. The manifold block may include a gas-delivery tube that extends into the donor container whenever the open top of the donor container is inserted into the opening of the manifold block. The tube blows air in a direction through the open top of the donor container, the opening in the manifold block, and into the recipient container to carry the organisms from the donor container to the recipient container.

The transfer device also may include a donor-container positioner and a recipient-container positioner for positioning the donor container and recipient container, respectively, at selected positions for facilitating the transfer of the organisms from the donor container to the recipient container. For example, in one mode of operation, the donor-container positioner is used to move the donor container to a first position for receiving the needle for anesthetizing the organisms and to a second position at the gas manifold to allow the organisms to be transferred to the recipient container. Similarly, the recipient-container positioner is used to position the recipient container at the gas manifold for receiving the organisms from the donor container.

The apparatus also may include a robotic apparatus, such as a robotic arm, for moving the donor and recipient containers to selected positions in three-dimensional space. In one mode of operation, for example, the robotic arm is used to pick up the donor and recipient containers at selected positions in respective container rack(s) and transfer the donor and recipient containers to the donor-container positioner and the recipient-container positioner, respectively, for transferring the organisms from the donor container to the recipient container. After the organisms are transferred to the recipient container, the robotic arm picks up the donor and recipient containers and transfers the containers to selected positions in respective container rack(s).

According to another representative embodiment, an apparatus is configured to automatically transfer live organisms from a donor container to a recipient container. The apparatus desirably includes an anesthetizing mechanism configured to automatically expose the organisms to an anesthetic for immobilizing the organisms before they are transferred from the donor container to the recipient container. The apparatus also may include a gas manifold fluidly connectable to a gas source (e.g., a source of compressed gas). The gas manifold is configured such that, whenever the donor and recipient containers are positioned at the gas manifold and gas is supplied to the gas manifold, a flow of gas is introduced into the donor container such that the organisms are transferred by the gas into the recipient container.

According to yet another representative embodiment, an apparatus for transferring live organisms from a donor container to a recipient container comprises a gas manifold fluidly connectable to a source of compressed gas. The gas manifold is configured such that, whenever the donor container and the recipient container are positioned at the gas manifold and the source of compressed gas is activated to supply gas to the gas manifold, gas is introduced into the donor container such that the organisms are blown by the gas into the recipient container.

According to still another representative embodiment, an apparatus is provided for transferring populations of live organisms contained in donor containers to corresponding recipient containers. A robotic arm is provided for picking up donor and recipient containers and transferring the containers to a transfer device. The transfer device is operable to automatically transfer insect populations from donor containers to respective recipient containers.

According to another representative embodiment, an apparatus for automatically transferring live organisms from a donor container to a recipient container comprises means for temporarily immobilizing the organisms in the donor container and means for transferring the organisms from the donor container to the recipient container after the organisms have been immobilized.

A method for transferring live organisms from a donor container to a recipient container, according to one embodiment, comprises temporarily immobilizing the organisms in the donor container by exposing the organisms to an anesthetic, such as by injecting an anesthetic gas into the donor container with a needle. After immobilizing the organisms, the organisms are transferred from the donor container to the recipient container. In one specific approach, transferring the organisms to the recipient container is accomplished by blowing the immobilized organisms from the donor container to the recipient container using flowing gas.

In an alternative method, a method for transferring live organisms from a donor container to a recipient container comprises positioning the donor container and the recipient container such that the open top of the donor container is adjacent the open top of the recipient container. A flow of gas is introduced into the donor container such that the organisms are carried by the gas to the recipient container.

These and other features of the invention will be more fully appreciated when the following detailed description of the invention is read in conjunction with the accompanying drawings.

BRIEF DESCRIPTION OF THE DRAWINGS

FIGS. 9A–9I are respective portions of a flow diagram of a program according to one embodiment for operating the apparatus of FIG. 1.

DETAILED DESCRIPTION

The methods for transferring insect populations from respective donor containers to respective recipient containers using the apparatus described herein may be implemented in software stored on a computer-readable medium and executed on a general-purpose computer. For clarity, only those aspects of the software germane to the invention are described; product details well-known in the art are omitted. For the same reason, the computer hardware is not described in further detail. In addition, the software can be implemented as hardware. It should thus be understood that the invention is not limited to any specific computer language, program or computer.

Figure 1:
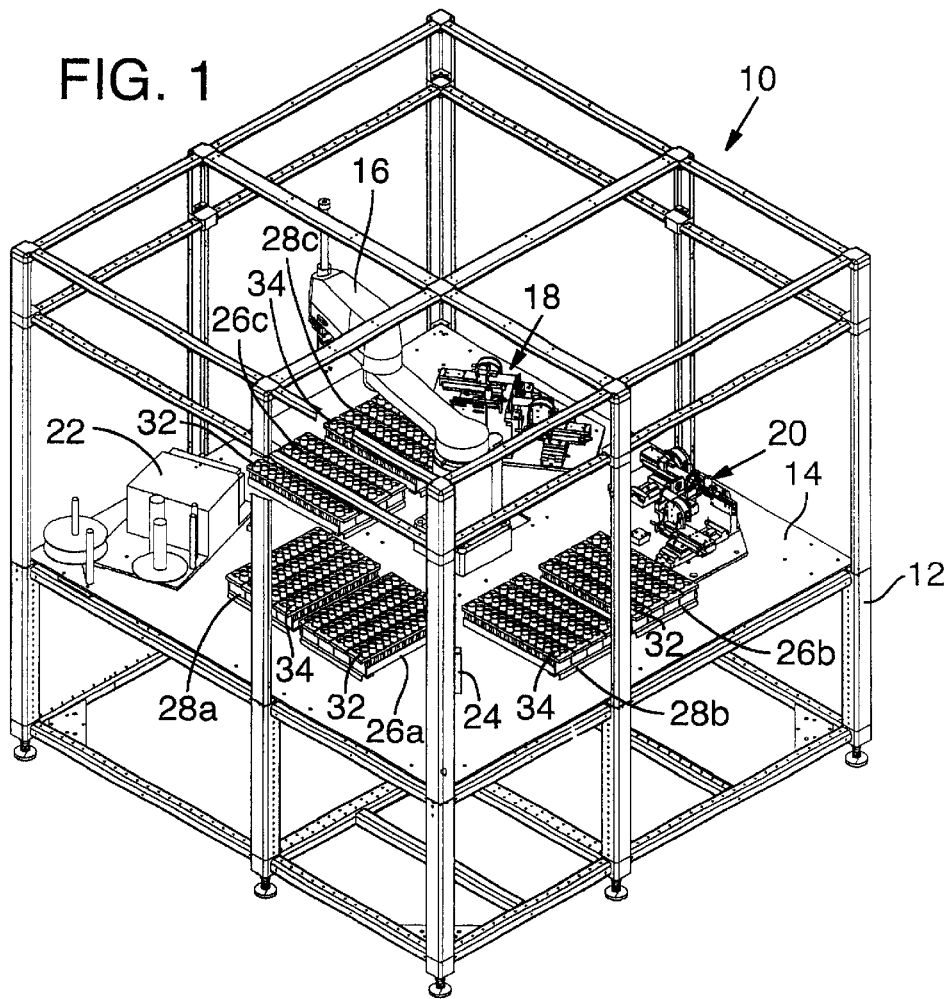
FIG. 1 is a perspective view of an apparatus according to one embodiment for maintaining a collection of organisms, such as fruit flies.
Figure 2:
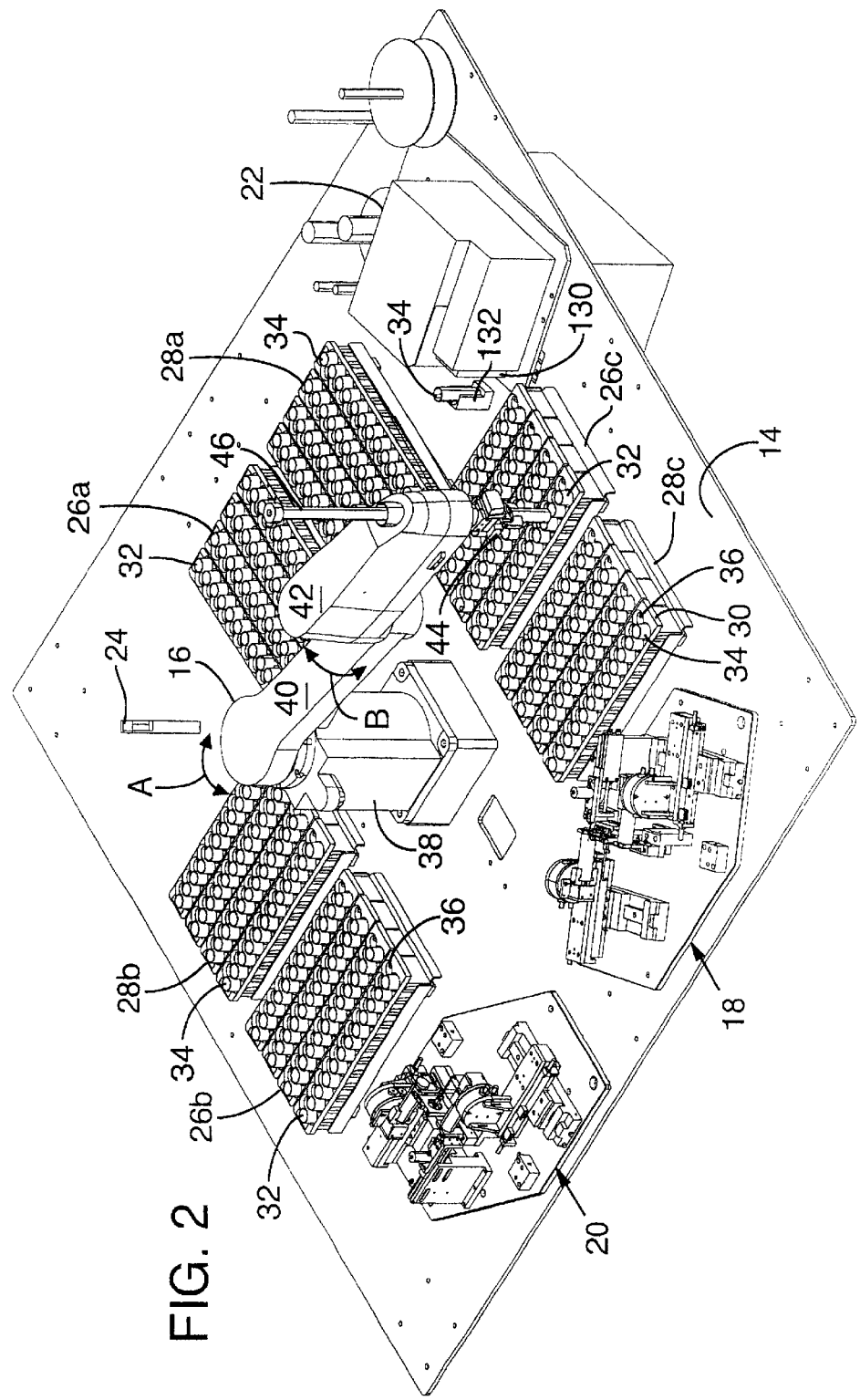
FIG. 2 is an enlarged perspective view of the apparatus of FIG. 1 with the support frame of the apparatus removed for clarity.

Referring initially to FIGS. 1 and 2, there is shown an apparatus, indicated generally at 10, according to one embodiment for maintaining a collection of small organisms. One exemplary use of the apparatus 10 is for maintaining stocks of insects, and in particular, stocks of fruit flies. Accordingly, by way of example, the following description proceeds with reference to maintaining a collection of fruit fly stocks. However, the apparatus also can be used to maintain stocks of any of various other organisms, such as arachnids or plant embryos.

The apparatus 10 performs various functions, one of which is the automatic transfer of live flies from donor vials, or containers, 32 to corresponding recipient vials, or containers, 34, such as for the purpose of feeding the flies. However, the apparatus 10 can be used to transfer flies or other organisms from a donor container to a recipient container for purposes other than for feeding the organisms. For example, the apparatus 10 can be used to separate adult flies from a population of eggs, larva, pupae and adult flies, as further described below. In addition, the apparatus 10 can be used to transfer plant embryos from a donor container to a recipient container. In the case of plant embryos, the apparatus and methods described herein for anesthetizing organisms prior to being transferred would not be needed.

The apparatus 10 in the illustrated configuration comprises a frame 12 (FIG. 1) that supports a platform 14 (FIGS. 1 and 2). Disposed on the platform 14 are first, second, and third donor trays, or pallets 26a, 26b, and 26c, respectively, and first, second, and third recipient trays, or pallets 28a, 28b, and 28c, respectively. As shown, each donor tray 26a, 26b, and 26c is positioned adjacent a corresponding recipient tray 28a, 28b, and 28c, respectively. Each donor tray 26a, 26b, and 26c supports a plurality of vial racks 30, each of which defining a plurality of openings 36 (FIGS. 2 and 2A) for receiving respective donor vials 32 that contain a donor population (e.g., eggs, larvae, pupae, and/or adult flies). Each recipient tray 28a, 28b, and 28c supports a plurality of vial racks 30 for supporting a plurality of recipient vials 34 in respective openings 36. The recipient vials 34 contain supplies of fresh food for the respective populations to be transferred into the recipient vials 34.

The platform 14 also supports a robotic arm 16 for moving donor and recipient vials 32, 34, respectively, to selected positions on the platform 14, and first and second transfer stations 18, 20, respectively, for transferring flies from respective donor vials 32 to corresponding recipient vials 34, as described in greater detail below.

The donor vials 32 may be provided with suitable indicia, such as respective bar-code labels 136 (FIG. 2A), for identifying or describing the donor populations. In one approach, for example, a bar-code label 136 identifies a specific "stock" number of a respective donor vial 32. The stock number of a donor vial can correspond to the position of the donor vial 32 in its respective rack 30 and/or to the particular genotype of the flies contained in the donor vial 32.

As shown in FIGS. 1 and 2, an optional label maker 22 may be provided for making bar-code labels and for applying the labels to recipient vials 34, as described in greater detail below. In addition, an optional, fixed bar-code scanner 24 (so named because it is positioned at a fixed location in the platform 14) may be provided for reading the bar-code labels 136 on donor and recipient vials, 32, 34, respectively.

Figure 2A:
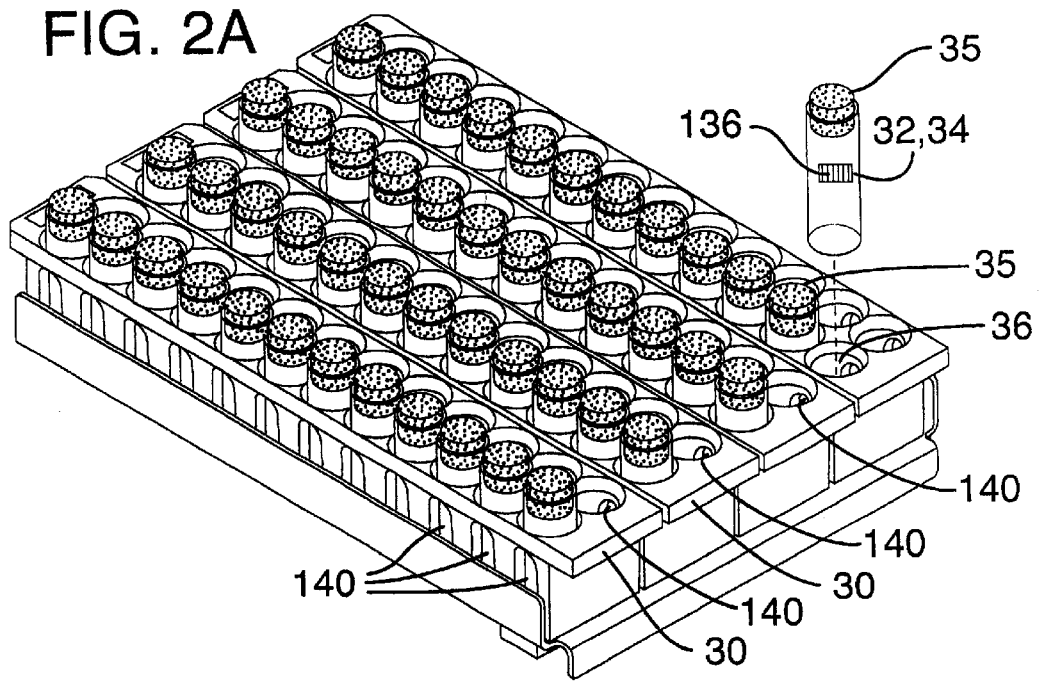
FIG. 2A is an enlarged perspective view of a tray of vials used in the apparatus of FIG. 1, the tray supporting a plurality of vial racks, each supporting a plurality of vials.

In the embodiment shown, each donor tray 26a, 26b, and 26c supports four vial racks 30, and each recipient tray 28a, 28b, and 28c supports four vial racks 30. As best shown in FIG. 2A, each vial rack 30 is formed with a 2×12 array of openings 36 for supporting a total of 24 vials (either donor vials 32 or recipient vials 34). For carrying out the transfer method described below, donor vials 32 and recipient vials 34 are placed in only one row of openings 36 of each vial rack 30. Thus, a total of 48 donor vials is associated with each donor tray 26a, 26b, and 26c, and a total of 48 recipient vials is associated with each recipient tray 28a, 28b, and 28c. For each donor vial 32 there is a corresponding recipient vial 34 with a supply of fresh food into which flies from the respective donor vial 32 are transferred. As shown in FIG. 2A, a respective plug 35 is inserted into the open top of each donor and recipient vial 32, 34, respectively, for restraining the contents of the vials. The plugs 35 desirably comprise a fibrous, air-permeable material, as commonly used in the art, or are otherwise perforated to expose the flies to atmospheric air.

As further shown in FIG. 2A, a plurality of windows or apertures 140 are formed in each side wall of the vial racks 30. The windows 140 are positioned adjacent respective openings 36 in the vial racks 30. Thus, the contents of each vial 32,34 in a vial rack 30 can be easily inspected by lifting the vial rack 30 from its respective tray to permit visual inspection of the vials via the windows 140 on both sides of the vial rack. Consequently, considerable time is saved in inspecting the vials because individual vials do not have to be removed from their respective vial racks for inspection.

Figure 8:
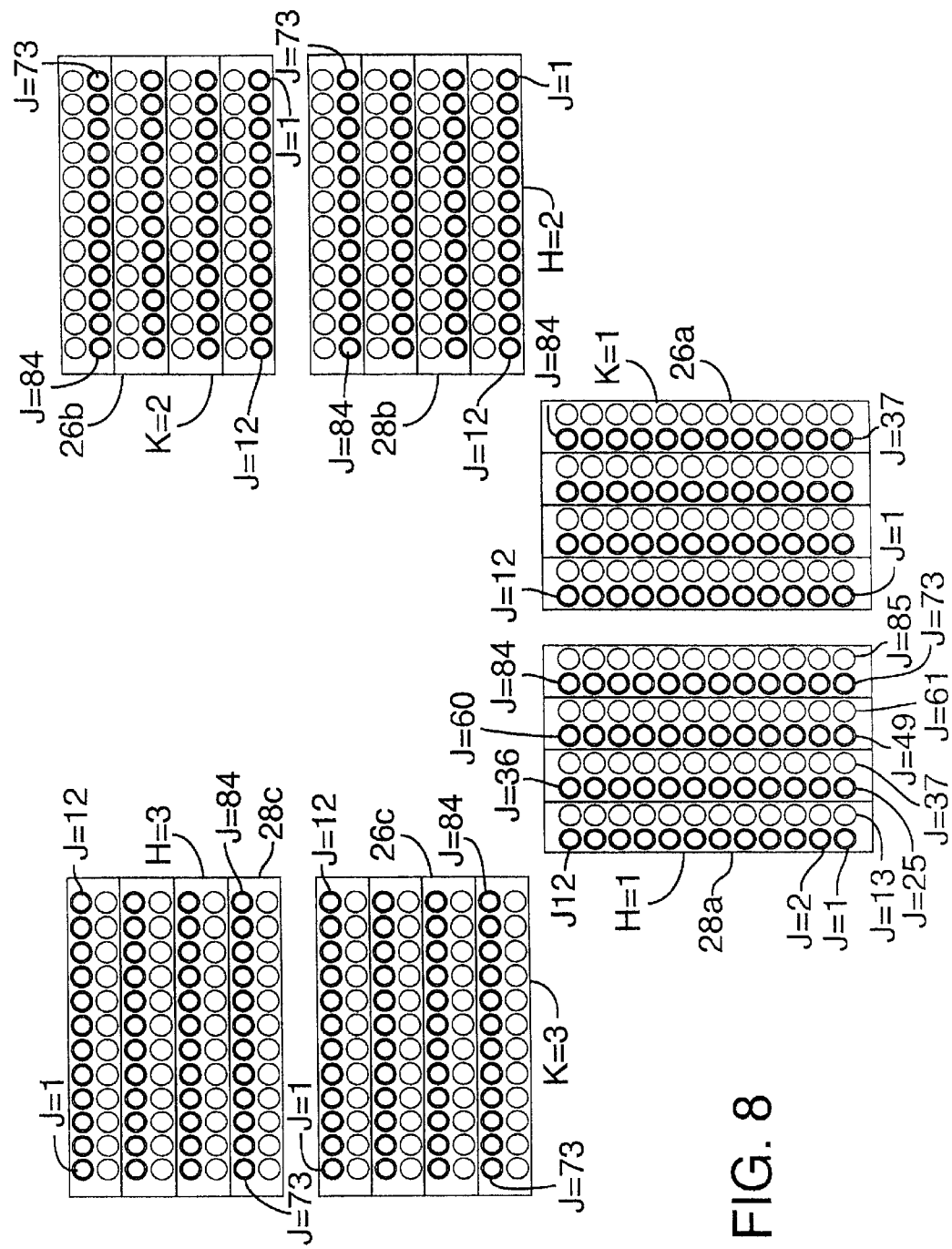
FIG. 8 is an enlarged, top plan view of the donor and recipient trays of the apparatus of FIGS. 1 and 2, showing respective numbering of the donor trays, recipient trays, donor vials, and recipient vials for purposes of operating the apparatus as detailed in FIGS. 9A–9I.

As shown in FIG. 8, for purposes of illustrating the operation of the apparatus 10, the first donor tray 26a may be identified by a tray-identification number K=1; the second donor tray 26b may be identified by a tray-identification number K=2; and the third donor tray 26c may be identified by a tray-identification number K=3. Similarly, the first recipient tray 28a may be identified by a tray-identification number H=1; the second recipient tray 28b may be identified by a tray-identification number H=2; and the third recipient tray 28c may be identified by a tray-identification number H=3.

Within each donor tray 26a, 26b, and 26c, the openings 36 of the vial racks 30 are identified by a "cell" number J=1 to J=96. Similarly, within each recipient tray 28a, 28b, and 28c, the openings 36 are identified by a "cell" number J=1 to J=96. Within each donor tray and recipient tray, the "occupied" openings 36 (i.e., openings 36 in which there is inserted a donor vial 32 or recipient vial 34) are identified by cell numbers J=1 to J=12, J=25 to J=36, J=49 to J=60, and J=73 to J=84. The "unoccupied" openings 36 (i.e., openings 36 that do not contain a donor vial 32 or a recipient vial 34) of each donor and recipient tray are identified by cell numbers J=13 to J=24, J=37 to J=48, J=61 to J=72, and J=85 to J=96. Each doner and recipient tray is supported at known respective coordinates on the platform 14. Thus, by specifying the cell number and the tray-identification number of the cell, the coordinates and, hence, the position of that cell may be determined.

Referring to FIG. 2, the robotic arm 16 has a vial manipulator 44 for moving donor vials 32 and recipient vials 34 to selected positions in three-dimensional space. For example, the robotic arm 16 may be used to pick up donor and recipient vials 32, 34, respectively, at selected cell positions and transfer the vials to either the first or second transfer station 18, 20 for transferring the flies of the donor vial 32 to the recipient vial 34. Following such a transfer step, the robotic arm 16 may be used to pick up the donor and recipient vials 32, 34, respectively, and transfer the vials to selected cell positions.

In any event, as shown in FIG. 2, the illustrated robotic arm 16 includes an upwardly extending base 38 that desirably is located at about the geometric center of the platform 14. A first arm portion 40 is rotatably coupled at one end to the upper end of the base 38 so that the first arm portion 40 is rotatable with respect to the base 38 in a horizontal plane above the platform 14, as indicated by double-headed arrow A. Coupled to the distal end of the first arm portion 40 is a second arm portion 42, which is rotatable with respect to the first arm portion 40 and the base 38 in a respective horizontal plane above the platform 14, as indicated by double-headed arrow B. The vial manipulator 44 is coupled to the lower end of a slide rod 46 extending through the distal end of the second arm portion 42 (i.e., the end opposite the first arm portion 40). The slide rod 46 is vertically movable with respect to the second arm portion along a vertical z-axis 56 (FIG. 3) to raise and lower the vial manipulator 44 to selected z-axis positions above the platform 14. The slide rod 46 also may be operable to rotate about the z-axis 56 for causing rotation of the vial manipulator 44 about the same axis.

Suitable drive mechanisms (e.g., servomotors) are provided for independently moving the first arm portion 40, the second arm portion 42 and the slide rod 46. These drive mechanisms are conventional, and well known in the art. Control of the drive mechanisms to independently control rotation of the first and second arm portions 40 and 42, vertical movement of the slide rod 46, and rotation of the slide rod 46 is by a suitable controller (not shown), such as a general purpose computer, operatively connected to the drive mechanisms of the robotic arm 16. The construction of the controller, either as a hard-wired processor or as a software-driven processor, will be appreciated from the description of the operation of the apparatus 10 described below with reference to FIGS. 9A–9I.

Figure 3:
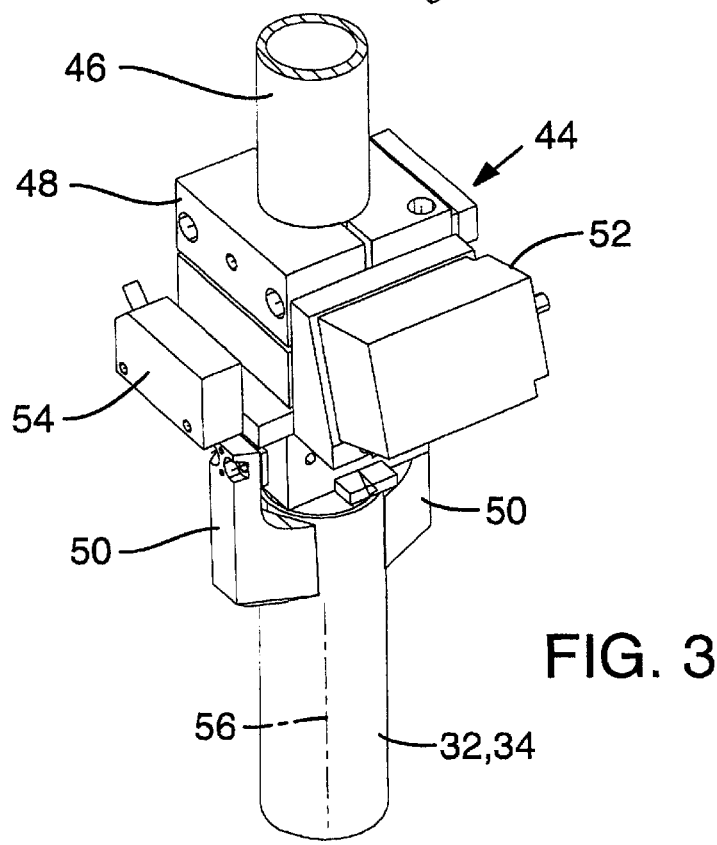
FIG. 3 is an enlarged perspective view of the vial manipulator of the robotic arm of FIGS. 1 and 2.

As best shown in FIG. 3, the vial manipulator 44 comprises a head 48 coupled to the lower end of the rod 46. Clamping jaws 50 are mounted underneath the head 48 and are configured to move toward and away from one another to clamp and release, respectively, the outer surface of a donor vial 32 or a recipient vial 34. The clamping jaws 50 may be covered with an inner elastomeric material to accommodate slight variations in vial diameter, and to provide greater frictional contact with the vials. Drive mechanisms for moving the clamping jaws 50 toward and away from one other are conventional and under the control of the controller (not shown). Also coupled to the head 48 are an optional, mobile bar-code reader, or scanner, 52 (so named because it can be moved to selected positions by the vial manipulator 44) and an optional sensor 54 for detecting the presence of a vial in certain cell positions in the donor and recipient trays. The sensor 54 may comprise, for example, a conventional photoelectric sensor. The bar-code reader 52 can be used to read bar-code labels 136 on donor and recipient vials 32, 34, respectively, and bar-code labels (not shown) on donor trays 26a, 26b, and 26c and recipient trays 28a, 28b, and 28c.

To pick up and move a vial with the vial manipulator 44, the robotic arm 16 is actuated to position the vial manipulator 44 above the vial. The vial manipulator 44 is lowered until a top portion of the vial is positioned between the clamping jaws 50, which are moved toward one another to secure the vial between the jaws 50. The vial manipulator 44 is then raised and moved to a new location on the platform 14 where the vial manipulator is lowered and the jaws moved away from one another to release the vial.

Figure 4:
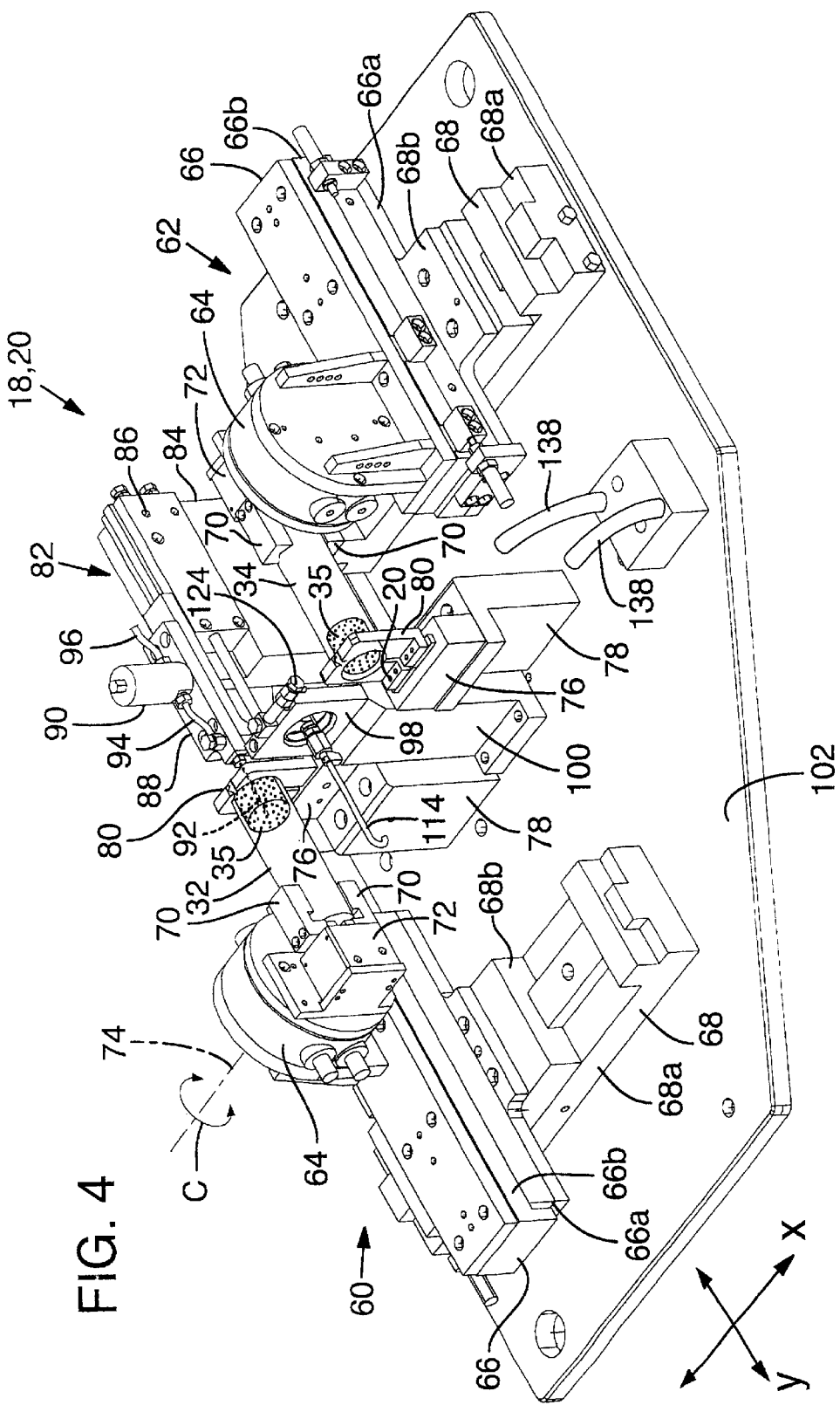
FIG. 4 is an enlarged perspective view of one of the transfer stations of the apparatus of FIGS. 1 and 2, showing a donor vial in position for receiving an anesthetic gas for temporarily immobilizing insects in the donor vial.

Referring now to FIG. 4, there is shown an enlarged view of one of the first and second transfer stations 18, 20 (also called a "transfer device" in other embodiments). Each transfer station 18, 20 in the illustrated configuration comprises a donor-vial positioner 60 and a recipient-vial positioner 62 mounted on a base 102. The donor-vial positioner 60 and the recipient-vial positioner 62 are configured to receive a donor vial 32 and a recipient vial 34, respectively, and position the donor vial 32 and the recipient vial 34 at selected positions within the transfer station.

The illustrated donor-vial positioner 60 comprises a rotatable actuator 64 mounted to, or otherwise carried by, a first slide 66. The first slide 66, in turn is mounted to or otherwise carried by a second slide 68. Clamping jaws 70 for gripping a donor vial 32 are coupled to a gripper body 72 mounted to a side of the rotatable actuator 64. The clamping jaws 70 are configured to move toward and away from one another to clamp and release, respectively, the outer surface of a donor vial 32. The clamping jaws 70 may be covered with an inner elastomeric material to accommodate slight variations in vial diameter, and to provide greater frictional contact with the vials.

The first and second slides 66, 68, respectively, are operable to position a donor vial 32 at selected x-y coordinates above the platform 14, the x-y axes being indicated in FIG. 4. The second slide 68 comprises a first portion 68a mounted to the base 102 and a second portion 68b that is movable with respect to the stationary portion 68a in the x-axis direction. The first slide 66 comprises a first portion 66a mounted on top of the second portion 68b of the second slide 68, and a second portion 66b that is movable in the y-axis direction relative to the first portion 66a. Thus, movement of the first portion 68b of the second slide 68 in the x-axis direction causes movement of the first slide 66 and the rotatable actuator 64 mounted thereon in the same direction, and movement of the second portion 66b of the first slide in the y-axis direction causes movement of the rotatable actuator 64 in the same direction.

The rotatable actuator 64 is operable to rotate about a horizontal axis 74, as indicated by double-headed arrow C, to rotate the clamping jaws 70 (with donor vial 32 within the clamping jaws 70), between an upright position and a substantially horizontal position, as shown in FIG. 4. Whenever the clamping jaws 70 are rotated to an upright position, a donor jar 32 may be positioned in or removed from the jaws 70 by the vial manipulator 44 on the robotic arm 16.

Any of various suitable drive mechanisms may be used to control the movements of the first slide 66, the second slide 68, the rotatable actuator 64, and the clamping jaws 70. In the illustrated embodiment, for example, the first slide 66, the second slide 68, the rotatable actuator 64, and the clamping jaws 70 are operatively connected to a compressed-gas source, such as a source of compressed air, via compressed-gas lines (not shown for clarity) for supplying compressed gas to respective pneumatic actuators (not shown) controlling the movements of these components. Other drive mechanisms, such as servomotors, also may be used to control the movements of the first slide 66, the second slide 68, the rotatable actuator 64, and the clamping jaws 70.

A plug-gripping mechanism 76, mounted on a riser 78, is positioned adjacent the donor-vial positioner 60 to assist in removing plugs 35 from respective donor vials 32 and subsequently replacing the plugs 35 back into their respective donor vials 32. The plug-gripping mechanism 76 comprises grippers 80 that are configured to move toward and away from one another to clamp and release, respectively, an outer surface portion of a plug 35 partially inserted into the open top of a donor vial 32. The movement of the grippers 80 to clamp and release a plug 35 may be effected by a pneumatic actuator controlled by compressed gas, or other suitable drive mechanism.

To remove a plug 35 from a donor vial 32, the rotatable actuator 64 is rotated about the axis 74 to place the donor vial in a horizontal position. The first slide 66 is actuated to move the donor vial 32 toward the plug-gripping mechanism 76 to position an outer surface portion of the plug 35 between the grippers 80, as shown in FIG. 4. The grippers 80 are moved toward one another to secure the plug 35 between the grippers 80, after which the first slide 66 is actuated to move the donor vial 32 in the opposite direction (i.e., away from the plug-gripping mechanism 76). As the donor vial 32 is moved away from the plug-gripping mechanism 76, the plug 35 is retained by the grippers 80. To insert the plug 35 back into the donor vial 32, the first slide 66 is actuated to move toward the plug-gripping mechanism 76 until the plug 35 is slidably inserted into the open top of the donor vial 32.

The construction of the recipient-vial positioner 62 is substantially identical to the construction of the donor-vial positioner 60. Thus, the recipient-vial positioner 62, like the donor-vial positioner 60, comprises a set of clamping jaws 70 for receiving a recipient vial 34. The clamping jaws 70 are coupled to a gripper body 72 mounted to a side of a rotatable actuator 64 for rotating the recipient vial 34 between an upright position and a substantially horizontal position, as shown in FIG. 4. The rotatable actuator 64 of the recipient-vial positioner 62 is carried by a first slide 66, which in turn is carried by a second slide 68, for moving the recipient vial 34 in the y-axis direction and the x-axis direction, respectively. Positioned adjacent the recipient-vial positioner 62 is a plug-gripping mechanism 76 mounted on a riser 78. The plug-gripping mechanism 76 has grippers 80 configured to clamp and release a plug 35 of the recipient vial 34 (as shown in FIG. 4). The recipient-vial positioner 62 may be operated in the same manner as the donor-vial positioner 60 for removing plugs 35 from respective recipient vials 34 and subsequently replacing the plugs 35 back into their respective recipient vials 34.

Each transfer station 18, 20 in the illustrated configuration includes an anesthetizing mechanism for automatically introducing an anesthetic into a donor vial 32 for temporarily immobilizing the flies in the donor vial 32. In the illustrated embodiment, for example, each transfer station 18, 20 includes a gas-handling system (also referred to herein as an "anesthetic-delivery system" in other embodiments), indicated at 82 (FIG. 4), configured to automatically introduce an anesthetic gas into a donor vial 32. The illustrated gas-handling system 82 comprises a riser 84 mounted to the base 102. A slide 86 is movably coupled to the riser 84 and is operable to move toward and away from an adjacent donor vial 32 in the y-axis direction. A needle 92 is supported in a substantially horizontal position by a top plate 88 of the slide 86. In FIG. 4, the needle 92 is shown extending into the plug 35 of the adjacent donor vial 32. A valve 90 (e.g., a solenoid valve), disposed on the top plate 88, is fluidly connected to the needle 92 via a gas line 94. A source of an anesthetic gas (not shown), such as $CO_2$, is fluidly connected to the valve 90 via a gas line 96. The valve 90 is operable to fluidly connect and disconnect the needle 92 to and from the source of the anesthetic gas.

For immobilizing the insects, any suitable anesthetic may be used. $CO_2$ is preferred because it is non-toxic, inexpensive, and easy to handle. However, other anesthetics, such as diethyl ether or an anesthetic known as FlyNap® (sold by Carolina Biological Supply Co.), alternatively may be used.

Alternative approaches may be used to expose a fly population in a vial to an anesthetic or to otherwise immobilize the flies. For example, an anesthetizing mechanism can be configured to place the top of a donor vial adjacent a nozzle connected to a source of an anesthetic gas to allow the gas to pass through the porous plug and into the donor container. In another approach, a robotic apparatus may be used to place a donor vial into an atmosphere of an anesthetic gas (e.g., a chamber filled with an anesthetic gas), or alternatively, a volatile liquid anesthetic (e.g., diethyl ether) may be poured on the porous plug of a donor vial. Still alternatively, a liquid anesthetic can be applied to an applicator wand made of absorbent material, which is then inserted into the donor vial.

Moreover, a fly population can be immobilized without the use of an anesthetic. For example, a donor container can be brought into thermal contact with a low temperature heat sink, or placed in a low-temperature atmosphere to expose the fly population to cold, which is effective to immobilize the flies.

In any event, to immobilize a population of flies in a donor vial 32 with the illustrated gas-handling system 82, the donor vial 32 is placed in the horizontal position with the plug 35 of the donor vial 32 being secured by the grippers 80 of the associated plug-gripping mechanism 76. The slide 86 is actuated to move the needle 92 in the y-axis direction to insert the needle 92 into the plug 35. Desirably, the needle 92 is inserted into the plug 35 but does not extend beyond the bottom of the plug 35 (as shown in FIG. 4). This prevents a channel or bore from being formed though the length of the plug 35 through which flies can escape. The valve 90 is then opened to allow the anesthetic gas to flow through the needle 92. Anesthetic gas flowing from the needle 92 permeates the plug 35 and enters the donor vial 32. The introduced anesthetic gas displaces the original atmosphere in the vial through the porous plug 25, thereby immobilizing the flies in the donor vial 32.

In alternative embodiments, the needle 92 can be inserted through the plug 35 until the distal end of the needle 92 extends beyond the bottom of the plug 35.

After the insect population is immobilized by the anesthetic gas, the valve 90 is closed and the needle 92 is withdrawn from the donor vial 32 by moving the slide 86 in the y-direction away from the donor vial 32. At this stage, the plug 35 can be removed from the donor vial 32 and the donor vial 32 can be moved into position for transferring the flies to a corresponding recipient vial 34, as further described below.

As further shown in FIG. 4, a gas manifold 98, supported on a riser 100, is positioned on the base 102 intermediate the donor-vial positioner 60 and the recipient-vial positioner 62. The gas manifold 98 is configured to direct the flow of a gas, such as air from a compressed source, into a donor vial 32 such that the flies are blown by the gas into a corresponding recipient vial 34. Alternatively, the gas manifold 98 may be fluidly connectable to a low-pressure gas source, such as from a blower or fan, for blowing the flies into a recipient vial. 34.

Figure 6:
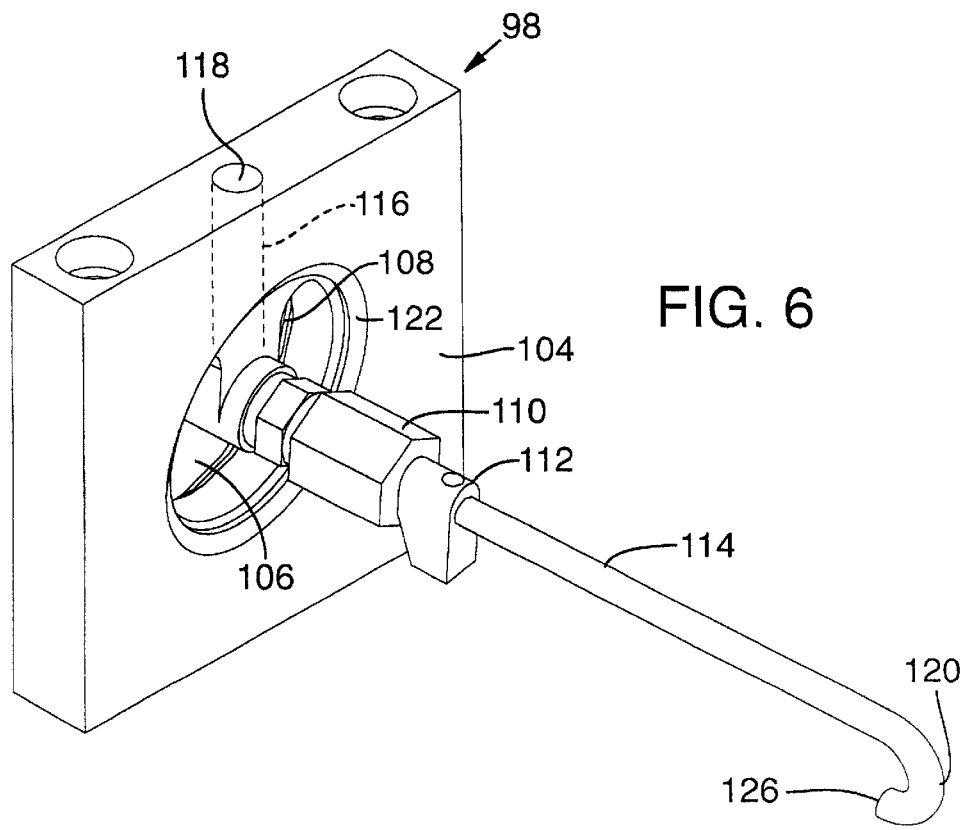
FIG. 6 is an enlarged perspective view of the gas manifold of FIGS. 4 and 5.

As best shown in FIG. 6, the illustrated gas manifold 98 comprises a manifold block 104 formed with a centrally located aperture, or passageway, 106. On each side of the manifold block 104, a recessed portion 122 circumscribes the passageway 106. The recessed portions 122 are dimensioned to permit the open top end of a vial to be at least partially inserted into the passageway 106. A tongue portion 108 extends downwardly from the top of the passageway 106, the bottom portion of the tongue portion 108 being coupled to a horizontally extending pneumatic fitting 110. The fitting 110 is connected to a holder 112 for holding a gas-delivery tube 114 in a substantially horizontally position.

The manifold block 104 is formed with an internal fluid passageway 116 that extends from an opening 118 in the top of the block to an opening (not shown) in the tongue portion 108. An inlet manifold 124 (FIG. 4) may be connected to the opening 118 for fluidly connecting a compressed-gas supply line (not shown) to the fluid passageway 116. The fluid passageway 116 is in fluid communication with a bore in the fitting 110 and a corresponding bore in the holder 112. Thus, gas introduced into the opening 116 flows through the passageway 116, the fitting 110, the holder 112, and the gas-delivery tube 114.

Figure 7:
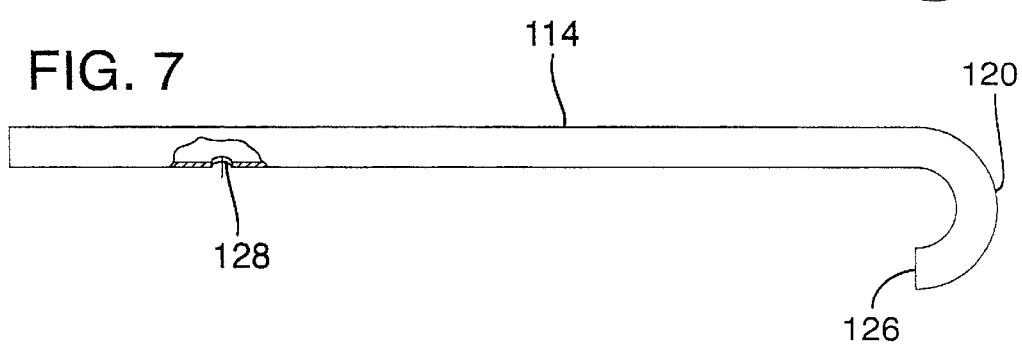
FIG. 7 is an enlarged side view of the gas-delivery tube shown in FIG. 6.

The gas-delivery tube 114 in the illustrated configuration has a first outlet opening 126 at a distal end thereof and a second outlet opening 128 (FIG. 7) situated proximate the holder 112 (FIG. 6). A distal end portion 120 of the gas-delivery tube 114 desirably is curved 180° so that gas exiting the first outlet opening 126 flows through the opening 106 and into a recipient vial 34 positioned on the opposite side of the manifold block 104.

To transfer a fly population from a donor vial 32 to a recipient vial 34, the flies desirably are first immobilized, as described above, and the plugs 35 of both the donor and recipient vials 32, 34, respectively, are removed from their respective vials in the manner described above. The donor-vial positioner 60 is actuated to move the donor vial 32 to a transfer position shown FIG. 5 in which the open top of the donor vial 32 is partially inserted into the passageway 106 of the manifold block 104 with the gas-delivery tube 114 being inserted into the donor vial 32. Similarly, the recipient vial holder 62 is actuated to move the recipient vial 34 to the transfer position in which the open top of the recipient vial 34 is partially inserted into the opposite side of the passageway 106.

Figure 5:
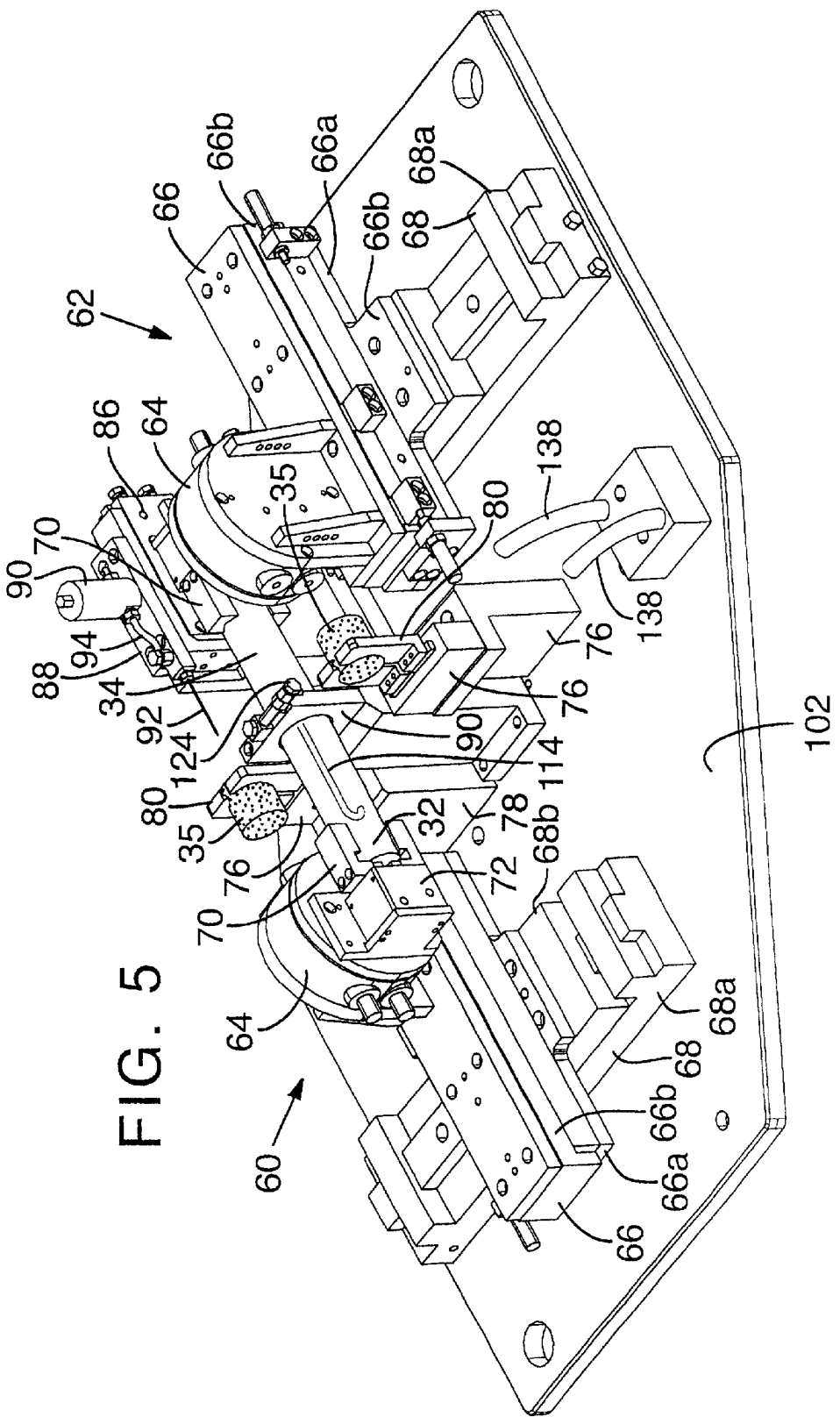
FIG. 5 is an enlarged perspective view of the transfer station of FIG. 4, showing the open tops of a donor vial and a recipient vial partially inserted into a gas manifold for transferring insects from the donor vial to the recipient vial.

After the donor and recipient vials 32, 34, respectively are properly aligned as shown in FIG. 5, flow of gas from the compressed gas source is activated to supply gas to the gas manifold. Gas exiting the first outlet opening 126 of the tube 114 (FIGS. 6 and 7) blows the flies from the donor vial 32 through the passageway 106 into the recipient vial 34. The second outlet opening 128 of the tube 114 directs a stream of gas toward the bottom of the donor vial 32 to assist in entraining the flies in the flow of gas as they are blown through the passageway 106.

The flow of gas into the donor container can be either a continuous flow or, alternatively, a rapid succession of short pulses of gas. In working embodiments, the latter approach was found to be most effective in transferring flies from a donor vial into a recipient vial.

After the flies are transferred to the recipient vial 34, the plugs 35 can be replaced in their respective vials. The vial manipulator 44 on the robotic arm 16 can then be used to remove the donor and recipient vials 32, 34, respectively, from the donor-vial positioner 60 and the recipient-vial positioner 62, respectively, for placement in selected cell positions of the donor and recipient trays.

As noted above, when raising fruit flies, a donor population typically includes pupae, larvae, and eggs. The pupae generally adhere to the inside surface of a donor vial; the eggs generally adhere to the inside of the donor vial and/or the food supply in the donor vial; and the larvae generally reside within the food supply in the donor vial. Consequently, the pressure at which the gas is delivered into the donor vial can be selected such that most, if not all, of the larvae, pupae and eggs in the donor vial 32 are not displaced into the recipient vial by the stream of gas. In working embodiments, 80 psig of compressed air delivered through the tube 114 was found to be sufficient to blow the flies of a donor population into a recipient container 34 without also blowing the eggs, larvae and pupae into the recipient container.

As shown in FIGS. 4 and 5, one or more compressed-gas conduits 138 may be provided at each transfer station 18, 20. The conduits 138 are fluidly connectable to a compressed-gas source (e.g., compressed air). The conduits 138 are operable to blow gas across the transfer station for blowing away any debris or organisms (e.g., food or flies) that may have escaped from either vial during a transfer process.

In addition, compressed-gas conduits (not shown) can be mounted at convenient locations for directing a flow of gas over the open tops of the donor vial 32 and the recipient 34 when the plugs 35 are removed from their respective vials. This prevents stray flies from entering either the donor vial 32 or the recipient vial 34 when the plugs 35 are removed from their respective vials. In one embodiment, a compressed-gas conduit is mounted on the donor-vial positioner 60 and the recipient-vial positioner 62, with each conduit configured to direct a flow of gas over the open top of an associated vial. The compress-gas conduits may comprise, for example, air knives configured to produce a curtain of air.

Referring again to FIGS. 1 and 2, the label maker 22 and a bar-code scanner 24 (also called a "bar-code reader") now will be described. The label maker 22 is operable to print bar-code labels and apply the labels to respective recipient vials 34. In the method described below, each recipient vial 34 desirably receives a label that is identical to the label of its corresponding donor vial 32. As best shown in FIG. 2, the label maker 22 includes an extendable tamp pad 130 for applying labels to recipient vials 34. Positioned in front of the tamp pad 130 is a vial holder 132 adapted to receive a recipient vial 34 intended to receive a label. The illustrated tamp pad 130 has a curved tamping surface that corresponds to the curvature of the recipient vials 34. The vial manipulator 44 of the robotic arm 16 may be used to place recipient vials 34 in the vial holder 132.

The label maker 22 operates in the following manner. After a label is printed by the label maker 22, the label is positioned on the tamp pad 130. Then, the tamp pad 130 extends outwardly toward the recipient vial 34 in the vial holder 132 to affix the label to the outside surface of the recipient vial 34.

The bar-code scanner 24 can be used to read the bar-code labels on donor vials 32 and/or recipient vials 34. For use of the bar-code scanner 24, a vial is picked up by the vial manipulator 44 and positioned so that the label on the vial can be read by the bar-code scanner 24. The bar-code scanner 24 automatically reads the bar code and relays this information to the controller (not shown) and/or the label maker 22. In the method described below, the bar-code scanner 24 can be used to identify the stock numbers of donor vials 32 so that identical bar-code labels can be printed and applied to their corresponding recipient vials 34 by the label maker 22.

In alternative embodiments of the apparatus 10, one or more cameras can be positioned at convenient locations (such as on the robotic arm 16 or on the platform 14) for counting the number of flies in a vial or for determining the specific make up of a particular fly population. For example, a camera can be used to determine the number of male and female flies in a fly population or to determine the number of flies carrying a specific chromosome. In the latter example, selected chromosomes can be marked with a bioluminescent marker to enable identification of the flies carrying those chromosomes.

In working embodiments, and by way of example, the robotic arm 16 comprises a model 850 SCARA robot, manufactured by Epson America, Inc. of Carson, Calif. The label maker comprises a Label-Aire model 2138 of Fullerton, Calif. The sensor 54 comprises a model PZ-V31 photoelectric sensor manufactured by Keyence Corp. of Woodcliff Lake, N.J. The mobile bar-code scanner 52 comprises a Keyence model BL-600HA and the fixed bar-code scanner 24 comprises a Keyence model BL-600.

FIGS. 9A–9I are a flow diagram illustrating in detail a program (either software or hard-wired program) according to one specific embodiment for operating the apparatus 10. In the program the apparatus 10 is used to perform multiple tasks including the transfer of flies from donor vials 32 to corresponding recipient vials 34, as well as providing new bar-code labels for the recipient vials 34.

In the flow diagrams several variables are specified by the operator and/or tracked by the program. For purposes of illustration, the variables discussed herein are with respect to the configuration shown in FIG. 8, in which there are three donor trays 26a, 26b, and 26c and three recipient trays 28a, 28b, and 28c. Each donor tray 26a, 26b, and 26c and recipient tray 28a, 28b, and 28c has 48 "occupied" cells or openings 36 and 48 "unoccupied" cell or openings 36. It will be recognized that the number of donor trays 26, recipient trays 28, donor vials 32, and recipient vials 34, as well as the particular arrays of vials shown in the figures, may be varied for other applications.

In any event, the variables referenced in the flow diagram are as follows:

1. "H" is a counter that represents the number of the current recipient tray from which recipient vials 34 are being taken;
2. "K" is a counter that represents the number of the current recipient tray from which donor vials 32 are being taken;
4. "J" is a counter that represents the number of the current respective cell positions of the donor tray K and recipient tray H and, if those cell positions are occupied, the number of the current donor and recipient vials in these cell positions; and
6. "F" is set by the operator as either 1 or 2; if F=1, then donor vials 32 are replaced into their original cell positions after transfer; and if F=2, then donor vials 32 are placed in unoccupied cell positions in recipient trays adjacent their corresponding recipient vials 34 after transfer.

Figure 9A:
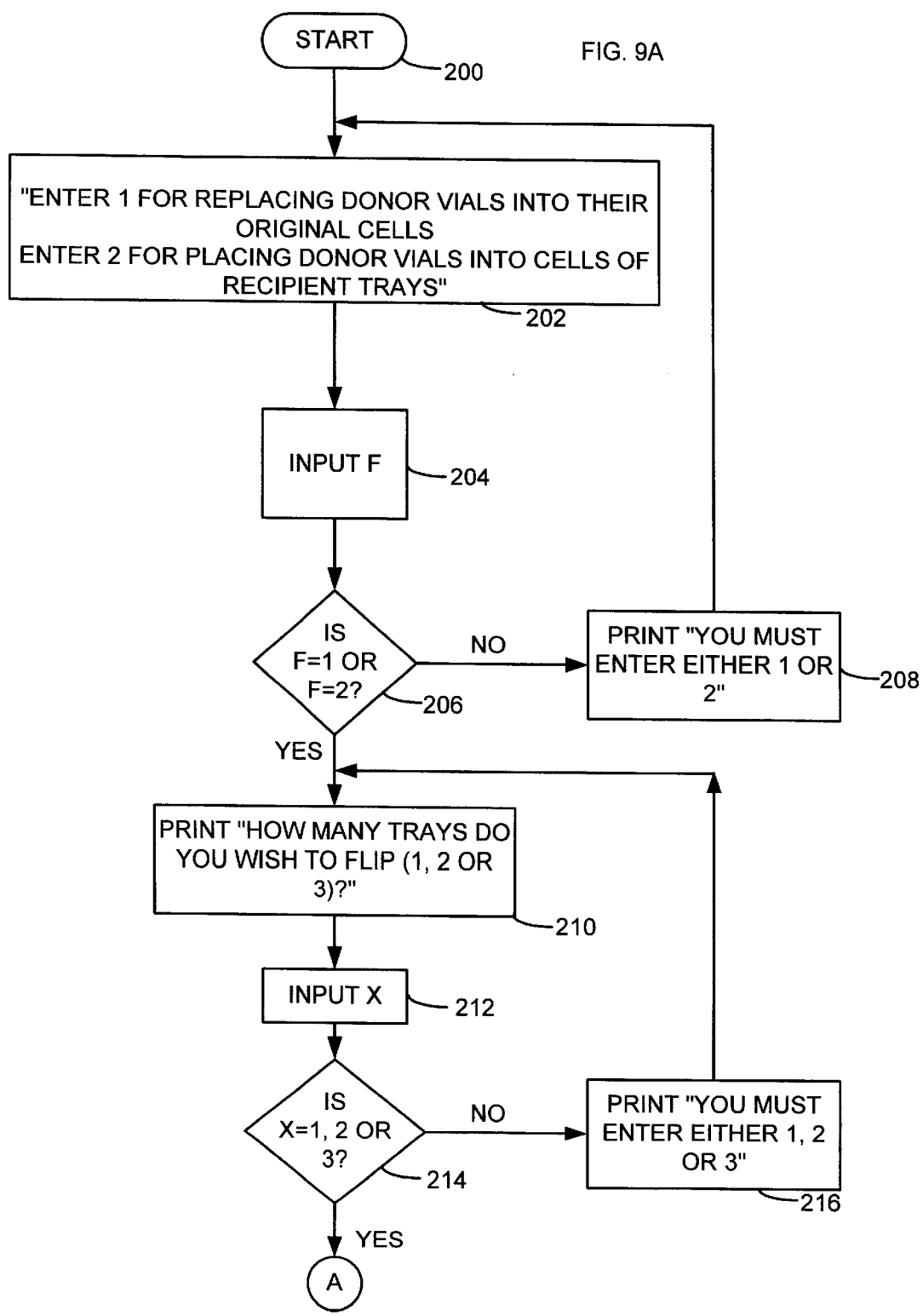

Referring initially to FIG. 9A, the program starts at block 200 and then proceeds to block 202, at which point the operator is prompted to select the manner in which empty donor vials 32 will be handled after their contents are transferred to corresponding recipient vials 34. The operator inputs the selection (either 1 or 2) at block 204 as a value for variable F. If the first option is selected (setting F=1), the donor vials 32 will be replaced into their original cell positions in their respective donor tray 26a, 26b, or 26c. However, if the second option is selected (setting F=2), then the donor vials 32 will be placed in respective unoccupied cell positions in recipient trays 28a, 28b, and 28c adjacent to their corresponding recipient vials 34. The program confirms at blocks 206 and 208 that a proper selection has been made.

At block 210 the program prompts the operator to select the number of available donor trays 26a, 26b, and 26c having donor vials 32 that need to be "flipped." As used herein, to "flip" a donor vial 32 means to transfer the fly population of the donor vial to a recipient vial 34. At block 212 the operator inputs the selection as a value for X (either 1, 2 or 3). The program confirms at blocks 214 and 216 that a proper selection has been made.

Figure 9B:
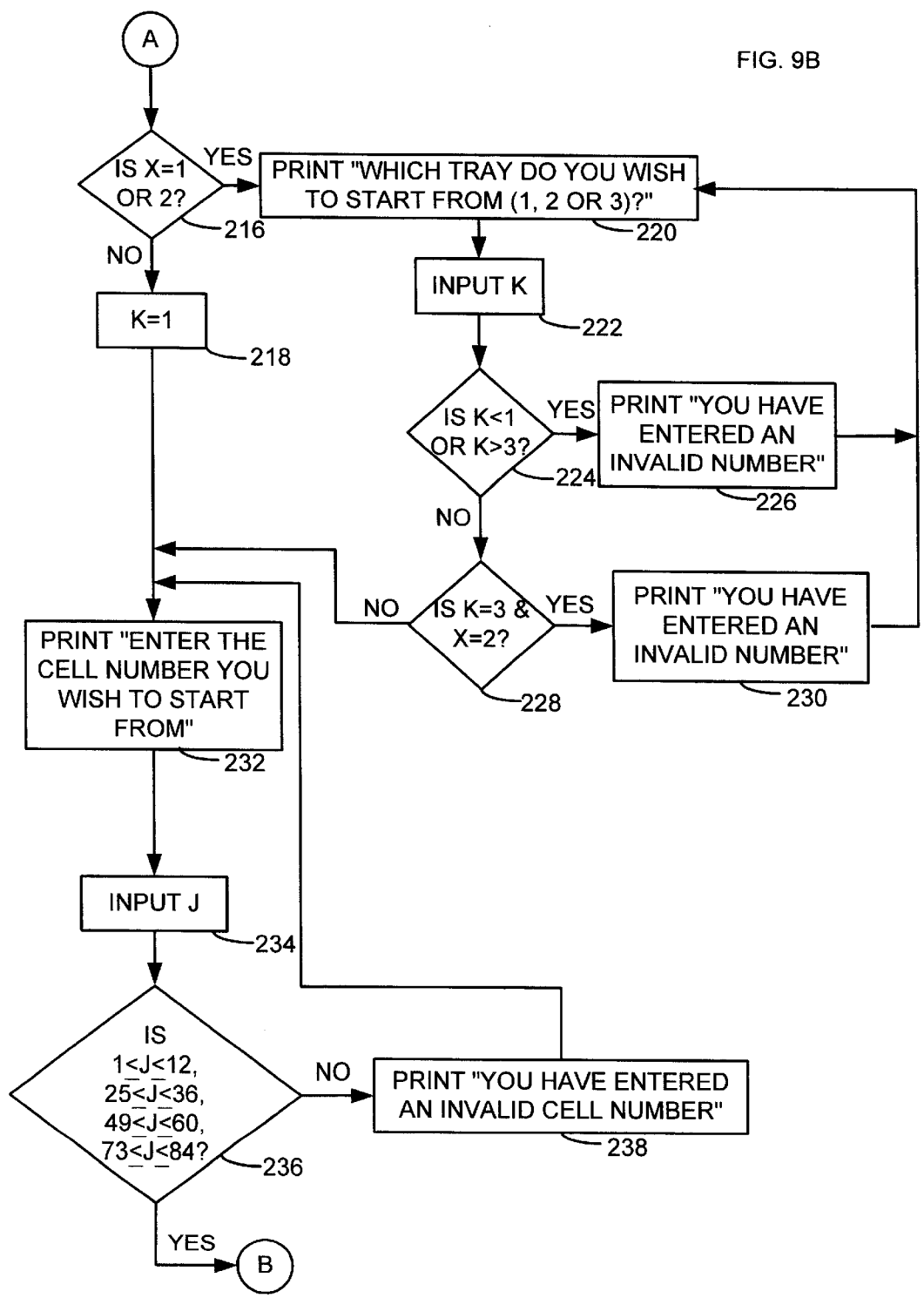

Referring to FIG. 9B, the program then proceeds to decision block 216. If X=1 or X=2, then the program at block 220 prompts the operator to select one of the donor trays 26a, 26b, or 26c (as 1, 2, or 3, respectively) as a starting position for the process, and to input that selection at block 222 as the initial value for K, the counter for the current donor tray. The program confirms, at blocks 224, 226, 228, and 230, that a proper selection has been made. If, at block 216, X≠1 or X≠2 (i.e., if X=3), then the program proceeds to block 218 for setting the value of K to 1.

At block 232, the program prompts the operator to select a specific cell position number for a donor vial 32 (of the donor tray K), as a starting position for the process and to input that selection, at block 234, as the initial value for J. As shown in FIG. 8, donor vials 32, in this example, are positioned in cells J=1 to J=12, J=25 to J=36, J=49 to J=60, and J=73 to J=84. Accordingly, the program confirms, at blocks 236 and 238 of FIG. 9B, that a proper value for J has been specified.

Figure 9C:
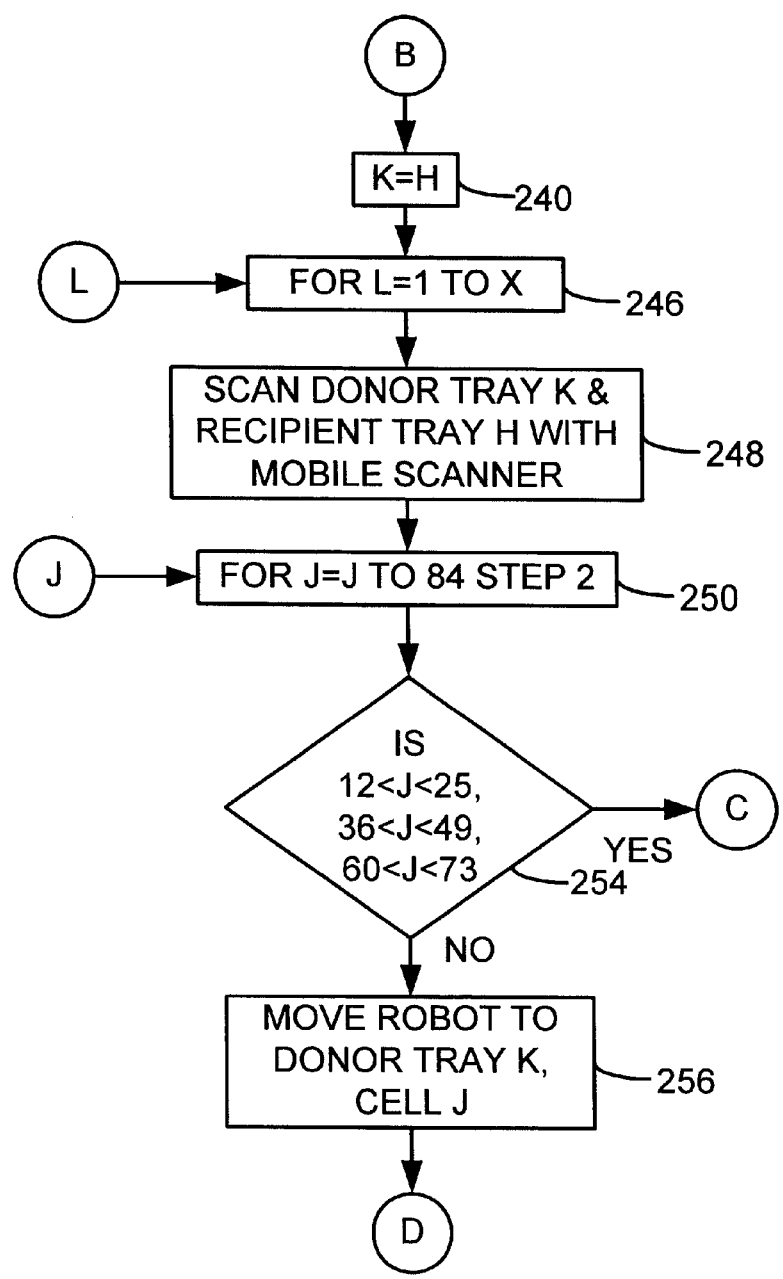

Referring to block 240 of FIG. 9C, the program initializes the value of H, the counter for the current recipient tray, so that H is equal to the current value of K. At block 246 the program provides a counter for repeating a main program loop, defined between block 246 and block 404 of FIG. 9I, for each donor tray K and recipient tray H (H=1 through X). At this stage the robotic arm 16 is activated to move the mobile bar-code reader 52 to donor tray H for scanning the bar-code label on donor tray H and then to recipient tray K for scanning the bar-code label on recipient tray K (block 248). At block 250 the program provides a counter for repeating an internal program loop, defined between block 250 and block 396 of FIG. 9I, until each donor vial 32 (J=1 through 84) in the current donor tray K is flipped.

At decision block 254 the program determines whether the current cell position number J is an occupied cell or an unoccupied cell. If at block 254 the value of J is equal to the cell number of an unoccupied cell (J=13 to J=24, J=37 to J=48, J=61 to J=72, or J=85 to J=96), then the program skips the internal program loop and instead proceeds to block 396 of FIG. 9I, at which point the program loops back to block 250 of FIG. 9C, at which the value of J is incremented by two. However, if at block 254 the value of J is equal to the cell position number of an occupied cell, the robotic arm 16 is activated to move the vial manipulator 44 to a starting position at donor tray K, cell J, as indicated at block 256.

Figure 9D:
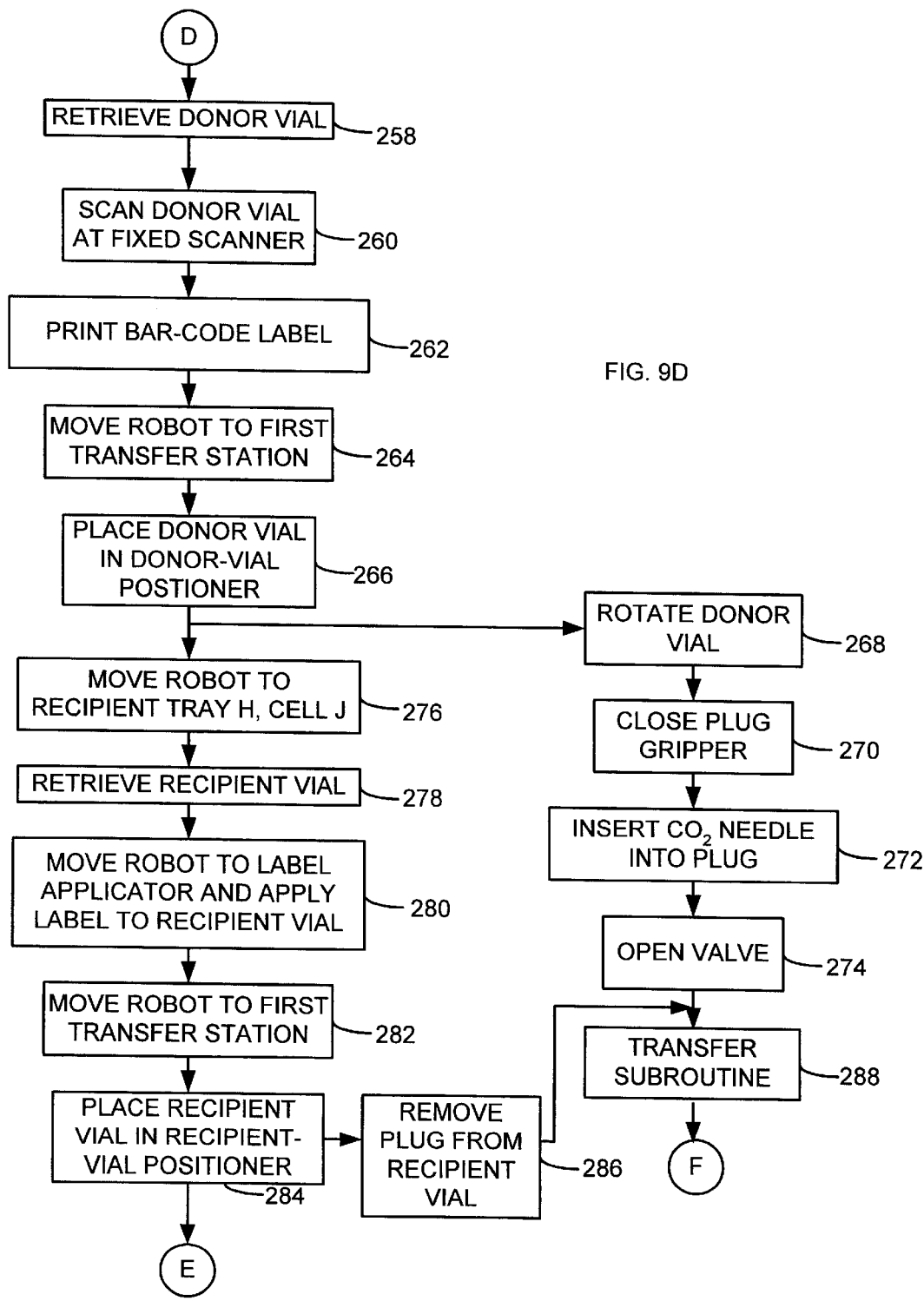

As indicated at block 258 of FIG. 9D, the vial manipulator 44 picks up donor vial J at cell J of donor tray K, and moves the donor vial to the fixed scanner 24 for reading the barcode label 136 on the donor vial so that the stock number of the donor vial can be identified (block 260). The stock-number information is sent to the label maker 22, which prints a bar-code label 136 that will be placed on the corresponding recipient vial J at cell position J of tray H (block 262). From the fixed scanner 24 the robotic arm 16 moves the donor vial J to the first transfer station 18, as indicated at block 264. The donor vial J is then lowered into the jaws 70 of the donor-vial positioner 60.

After the donor vial is placed in the donor-vial positioner 60, the donor-vial positioner 60 rotates the donor vial to a horizontal position (block 268) and moves the donor vial toward the plug-gripping mechanism 76 until the plug 35 of the donor vial is between the grippers 80 (as shown in FIG. 4). The grippers 80 are activated to close and thus clamp the plug 35 (block 270), and the slide 86 of the gas-handling system 82 is moved forwardly to insert the needle 92 into the respective plug 35 of the donor vial J (block 272) (as shown in FIG. 4). The valve 90 is then opened to allow an anesthetic gas (e.g., $CO_2$) to flow into the donor vial for a predetermined period of time (e.g., 17 seconds in this example)(block 274).

As the donor vial is moved into position, and as the needle 92 injects anesthetic gas into the donor vial (blocks 268, 270, 272, and 274), the robotic arm 16 moves the vial manipulator 44 to recipient tray H, cell J (block 276). The vial manipulator 44 is activated to pick up the recipient vial J at this cell position (block 278). The robotic arm 16 then moves the recipient vial J to the vial holder 132 so that the bar-code label 136 can be applied to the recipient vial J (block 280). After receiving the bar-code label, the robotic arm 16 moves the recipient vial J to the first transfer station 18 (block 282) where the recipient vial is placed in the jaws 70 of the recipient-vial positioner 62 (block 284). Optionally, the recipient vial J can be moved to the bar-code scanner 24 to confirm that the bar-code label placed on the recipient vial J is readable and accurate prior to being moved to the first transfer station 18.

After the plug 35 of the recipient vial J is removed (block 286), the program proceeds to the first transfer step, using a transfer subroutine indicated at block 288. The first transfer step operates to move the donor vial J and the recipient vial J to the compressed-gas manifold 98 (as shown in FIG. 5) where the flies of the donor vial J are transferred to the recipient vial J in the manner described above. Following the first transfer step, the program continues at blocks 312 and 320 of FIG. 9G, as described below.

Figure 9E:
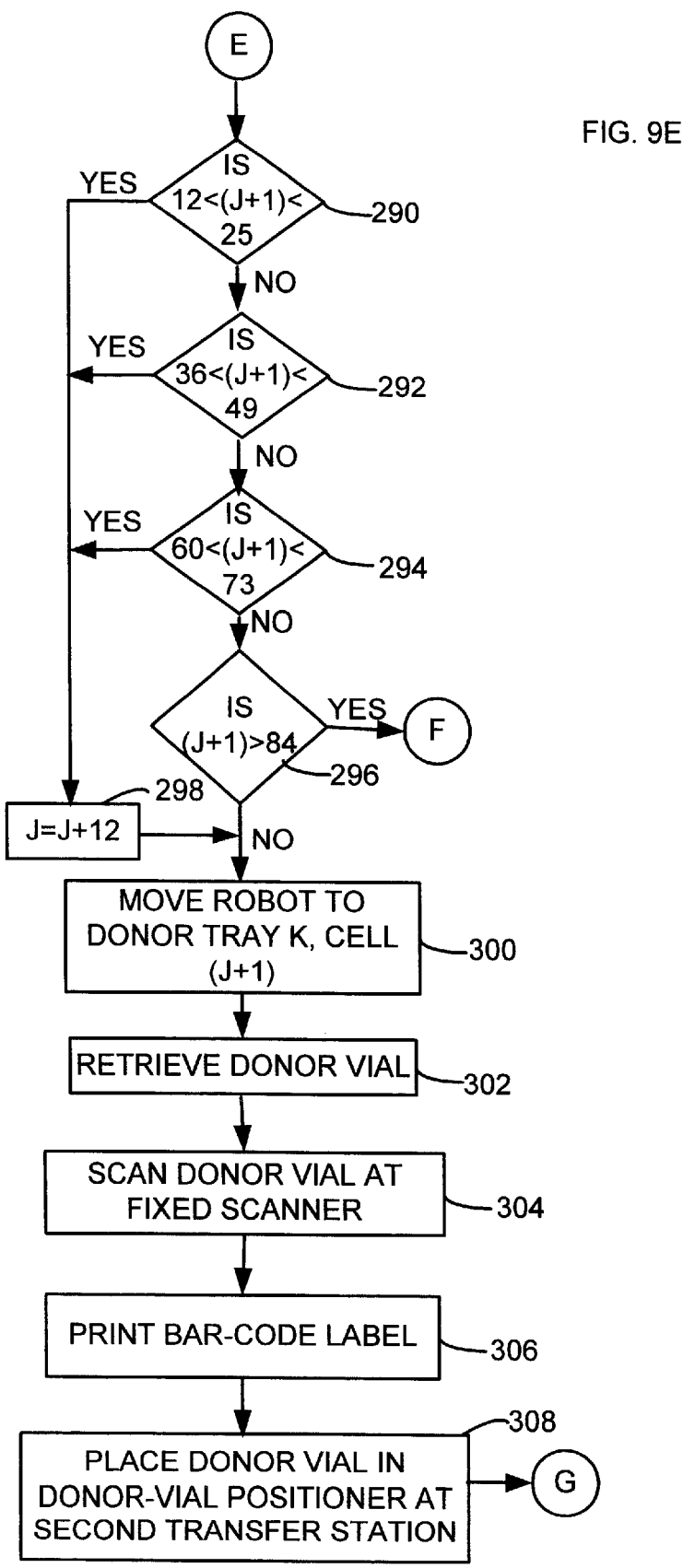
Figure 9F:
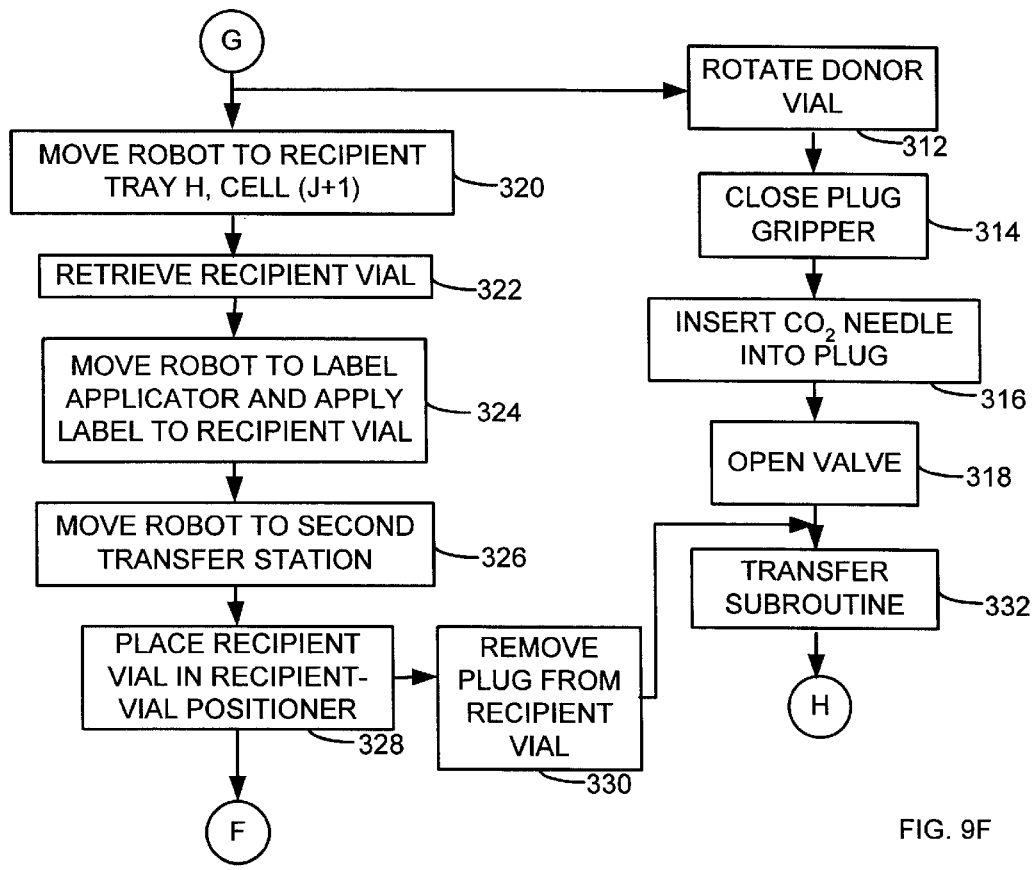

After the recipient vial J is placed in the recipient-vial positioner 62 at the first transfer station 18 (block 284 of FIG. 9D) and while the first transfer step is being carried out at the first transfer station 18, the program proceeds to the steps illustrated in FIGS. 9E and 9F for carrying out a transfer step at the second transfer station 20 for the donor vial 32 positioned in the next occupied cell. Referring then to FIG. 9E, the program first determines, at decision blocks 290, 292, and 294, whether the next cell position, J+1, is equal to the cell-position number of an unoccupied cell. If the value of J+1 is equal to the cell-position number of an unoccupied cell, then the programs increments the value of J by twelve (block 298) and proceeds to block 300. If, as determined at decision block 296, the value of J+1 is greater than 84, indicating that all of the donor vials 32 in tray K have been flipped, then the program continues at block 334 of FIG. 9G. If the value of J+1 is equal to the cell-position number of an occupied cell, then the program proceeds to block 300 (FIG. 9E) without executing the incrementing step of block 298.

At this stage the robotic arm 16 is operated to move the vial manipulator 44 to the donor vial J+1 in cell position J+1 of tray K (block 300; FIG. 9E), pick up the donor vial at this position (block 302), and move the donor vial to the fixed scanner 24 for reading the bar-code label on the donor vial (block 304). At block 306 the label maker 22 prints a bar-code label that will be placed on the corresponding recipient vial J+1 at tray H, cell J+1. From the fixed scanner 24 the robotic arm 16 moves the donor vial J+1 to the second transfer station 20 where the donor vial is placed in the associated donor-vial positioner 60 (block 308).

Referring to FIG. 9F, the donor-vial positioner 60 at the second transfer station 20 rotates the donor vial J+1 to a horizontal position and moves the donor vial toward the plug-gripping mechanism 76 to allow grippers 80 to close and secure the plug 35 of the donor vial (blocks 312 and 314). The needle 92 is then inserted into the respective plug 35 of the donor vial J+1 and the valve 90 is opened to allow the anesthetic gas to flow into the donor vial to immobilize the flies (blocks 316 and 318). In the meantime, the robotic arm 16 moves the vial manipulator 44 to the recipient vial J+1 at tray H, cell J+1 (block 320); the recipient vial J+1 is picked up by the vial manipulator 44 (block 322); the robotic arm 16 moves the recipient vial J+1 to the label maker 22 and the respective bar-code label is applied to the recipient vial (block 324); the robotic arm 16 moves the recipient vial J+1 to the second transfer station (block 326) where the vial is placed into the associated recipient-vial positioner 62 (block 328); and the plug 35 is removed from the recipient vial J+1 (block 330). If desired, the recipient vial J+1 can be moved to the bar-code scanner 24 to confirm that the bar-code label placed on the recipient vial J+1 is readable and accurate prior to being moved to the second transfer station 20.

When the recipient vial J+1 is positioned in the recipient-vial positioner 62 of the second transfer station 20, the program then executes a second transfer step, using the transfer subroutine (block 332), which operates to transfer the fly population of the donor vial J+1 to the recipient vial J+1.

Figure 9G:
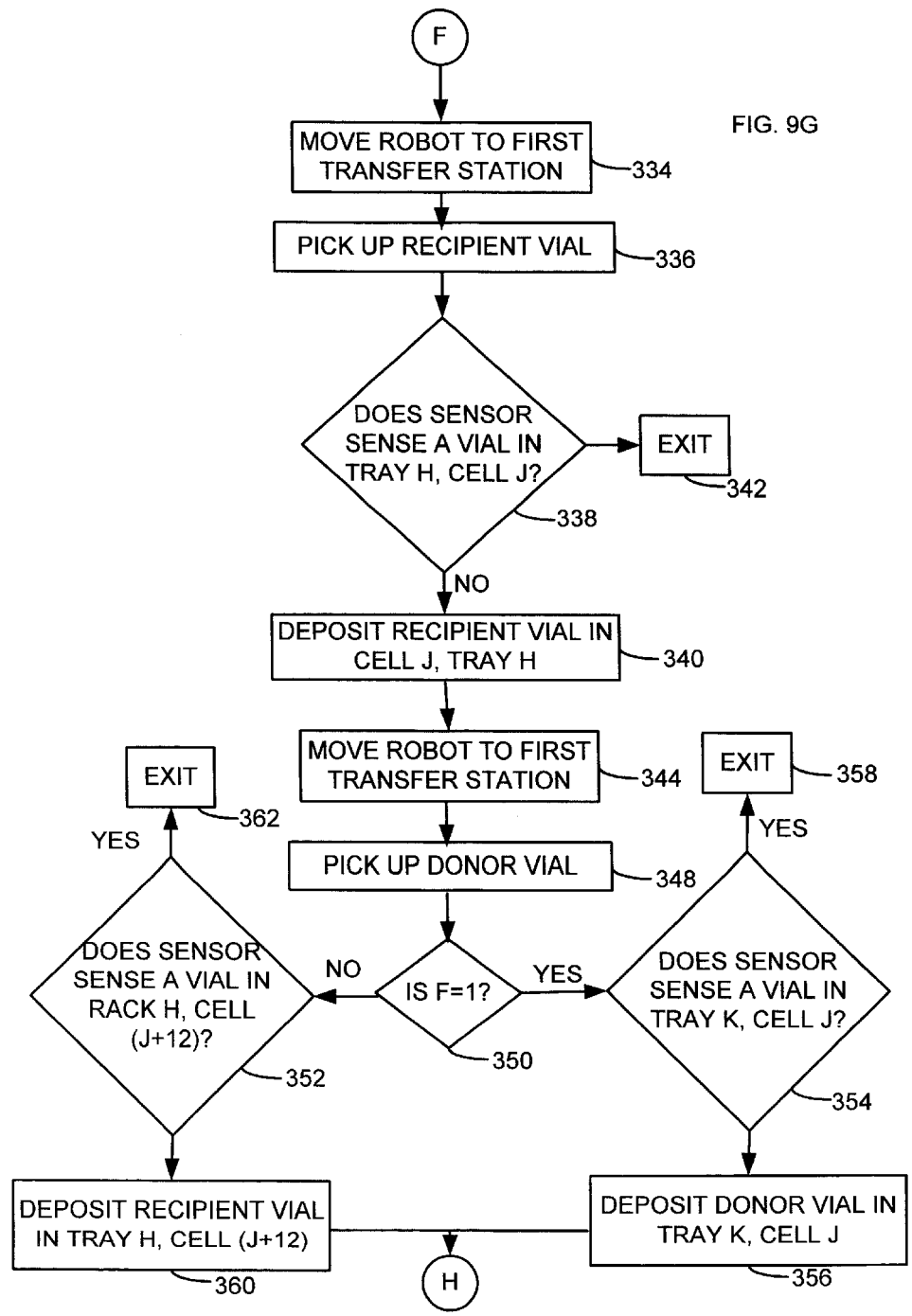

Following the first transfer step (block 288 of FIG. 9D), and while the second transfer step is being carried out at the second transfer station 20, the program executes the steps illustrated in FIG. 9G to return the donor vial J and the recipient vial J to selected respective positions in either donor tray K or recipient tray H. Referring to FIG. 9G, after the first transfer step is completed, the robotic arm 16 moves the vial manipulator 44 to a position above the recipient vial J in the recipient-vial positioner 62 of the first transfer station 18 (block 334), picks up the recipient vial J with the vial manipulator 44 (block 336), and moves the recipient vial J to a position just above tray H, cell J (the original cell position of recipient vial J) to allow the sensor 54 to detect for the presence of a vial in this position (block 338).

If the sensor 54 does not detect a vial in cell position J of tray H, then the recipient vial J is placed in this cell position (block 340). However, if the sensor 54 detects that a vial is already present in cell position J, tray H, which can occur as a result of operator error, then the program terminates at block 342. In this manner, damage to the vials can be avoided.

After the recipient vial J is returned to its cell, the robotic arm 16 moves the vial manipulator 44 to a position above the donor vial J in the donor-vial positioner 60 of the first transfer station 18 (block 344) and picks up the donor vial J with the vial manipulator 44 (block 348). If decision block 350 results in a determination that F=1, then the robotic arm 16 moves the donor vial J to a position just above its original cell (cell J of donor tray K) to allow the sensor 54 to detect for the presence of a vial in this position (block 354). However, if F=2, then the robotic arm 16 moves the donor vial J to a position just above cell J+12 of recipient tray H to allow the sensor 54 to detect for the presence of a vial in this position (block 352). In either case, if the sensor 54 detects that the respective cell is empty, then the donor vial J is placed in that cell (either cell J of tray K or cell J+1 of tray H) (blocks 356 and 360, respectively). However, if the sensor detects that a vial is present in either cell position, then the program is terminated (blocks 358 and 362).

Figure 9H:
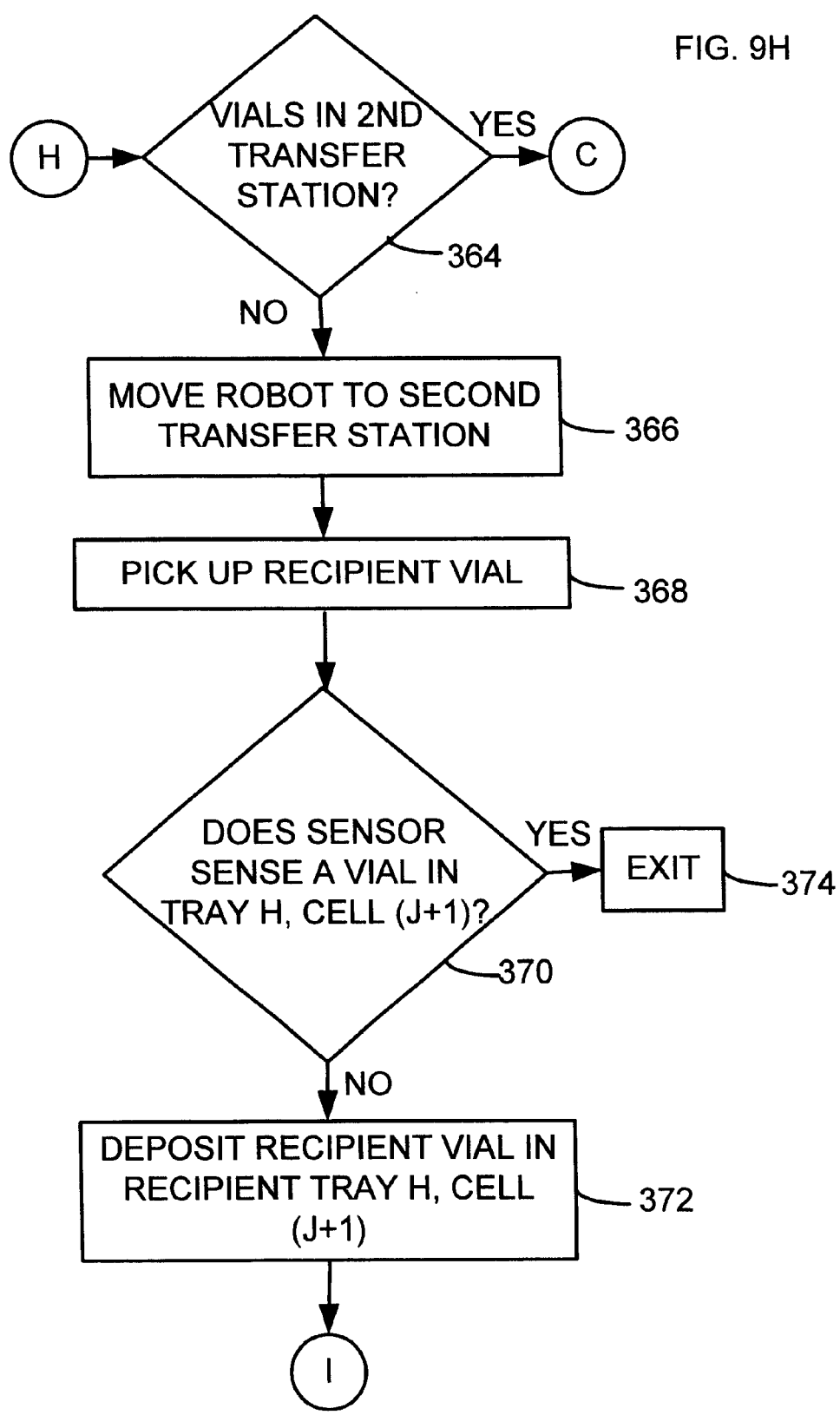

After placing the donor vial J in a respective cell position, the program proceeds to decision block 364 of FIG. 9H. As indicated at block 364, if no donor and recipient vials are present at the second transfer station 20 (which may be the case if donor vial J is the last donor vial of tray K), then the program proceeds to block 396 of FIG. 9I and then loops back to block 250 of FIG. 9C. On the other hand, if there are donor and recipient vials at the second transfer station 20, then the robotic arm 16 moves the vial manipulator 44 to the second transfer station 20 (block 366), picks up the recipient vial J+1 with the vial manipulator 44 (block 368), and moves the recipient vial J+1 to a position just above cell J+1 of tray H (the original cell position of recipient vial J+1) to allow the sensor 54 to detect for the presence of a vial in this position (block 370). If the sensor 54 detects that a vial is already present, then the program is terminated (block 374); otherwise, the recipient vial J+1 is lowered into cell position J+1 of tray H (block 372).

After the recipient vial J+1 is returned to its cell, the robotic arm 16 moves the vial manipulator 44 to the second transfer station 20 (block 378 of FIG. 9I) and picks up the donor vial J+1 with the vial manipulator 44 (block 380). If F=1, as indicated at decision block 382, then the robotic arm 16 moves the donor vial J+1 to a position just above its original cell (cell J+1 of donor tray K) to allow the sensor 54 to detect for the presence of a vial in this position (block 384). However, if F=2, then the robotic arm 16 moves the donor vial J+1 to a position just above cell J+13 of recipient tray H to allow the sensor 54 to detect for the presence of a vial in this position (block 390). In either case, if the sensor 54 detects that the respective cell is empty, then the donor vial J is placed in that cell (either cell J+1 of tray K or cell J+13 of tray H) (blocks 386 and 392, respectively). However, if the sensor detects that a vial is already present in either cell position, then the program is terminated (blocks 388 and 394).

At block 396 the program loops back to block 250 of FIG. 9C to increment the value of J by two, and the internal program loop (defined between block 250 and block 396) is repeated for the next two donor and recipient vials. The internal program loop is repeated until the fly population of each donor vial (J=1 to J=84) of the tray K is transferred into a corresponding recipient vial (J=1 to J=84) of tray H. Thereafter, the values of K and H are incremented at blocks 399 and 400, respectively, and the value of J is reset to 1 at block 402. At block 404 the program is caused to loop back to block 246 of FIG. 9C, at which point the value of L is incremented. The main program loop (defined between block 246 and block 404) is repeated for each donor and recipient tray (1 through X), that is, until L=X, after which the program ends, as indicated at block 406.

The present invention has been described with respect to particular embodiments and modes of action for illustrated purposes only. The present invention may be subject to many modifications and changes without departing from the spirit or essential characteristics thereof. We therefore claim as our invention all such modifications as come within the scope of the following claims.

We claim:

1. An apparatus for transferring small organisms from a donor container to a recipient container, the apparatus comprising:
   a source of an anesthetic configured to deliver anesthetic to the donor container for temporarily immobilizing the organisms in the donor container; and
   a source of gas configured to deliver a flow of the gas into the donor container sufficient for blowing the immobilized organisms from the donor container to the recipient container.

2. The apparatus of claim 1, further comprising an anesthetic-delivery system configured to automatically introduce the anesthetic into the donor container.

3. The apparatus of claim 2, wherein the anesthetic-delivery system comprises a needle fluidly connectable to the source of the anesthetic, the anesthetic-delivery system configured to insert the needle into the donor container for introducing the anesthetic into the donor container.

4. The apparatus of claim 1, further comprising a gas manifold configured to direct the flow of gas into the donor container such that the organisms are entrained and carried by the flow of gas into the recipient container.

5. The apparatus of claim 4, wherein the gas manifold comprises a manifold block defining an opening extending through the block, the opening being dimensioned to receive an open top portion of a donor container on one side of the block and an open top portion of the recipient container on the other side of the block such that, whenever the flow of gas is introduced into the donor container, the organisms are blown by the gas from the donor container through the opening into the recipient container.

6. The apparatus of claim 4, further comprising a transfer device comprising a donor-container positioner and a recipient-container positioner for positioning the donor container and recipient container, respectively, at the gas manifold for transferring the organisms from the donor container to the recipient container.

7. The apparatus of claim 1, further comprising a transfer device including an anesthetizing mechanism operatively coupled to the source of the anesthetic and a gas manifold operatively coupled to the source of gas, the anesthetizing mechanism being configured to introduce the anesthetic into the donor container, and the gas manifold being configured to blow the organisms by the flow of gas from the donor container to the recipient container.

8. The apparatus of claim 7, further comprising a robotic arm configured to move the donor and recipient containers to the transfer device for transferring the organisms from the donor container to the recipient container.

9. The apparatus of claim 1, wherein the anesthetic comprises carbon dioxide gas.

10. An apparatus for transferring live organisms from a donor container to a recipient container, the apparatus comprising:
    a transfer device for automatically transferring the live organisms from the donor container to the recipient container; and
    an anesthetizing mechanism configured to expose the organisms to an anesthetic so as to immobilize the organisms for transfer from the donor container to the recipient container.

11. The apparatus of claim 10, wherein:
    the donor container is a donor vial having a removable plug and the recipient container is a recipient vial: and
    the apparatus is configured to remove the plug from the donor vial, transfer the live organisms to the recipient vial, and place a removable plug in the recipient vial.

12. The apparatus of claim 10, wherein the anesthetic comprises carbon dioxide gas.

13. The apparatus of claim 10, wherein the anesthetizing mechanism comprises a needle fluidly connectable to a source of the anesthetic, the anesthetizing mechanism being configured to insert the needle into the donor container and deliver the anesthetic to the organisms in the donor container whenever the source of the anesthetic is activated to supply the anesthetic to the needle.

14. The apparatus of claim 10 configured such that the anesthetizing mechanism exposes the organisms to the anesthetic so as to immobilize the organisms prior to transferring the organisms from the donor container to the recipient container.

15. The apparatus of claim 10, wherein the anesthetizing mechanism is configured to automatically expose the organisms to the anesthetic so as to immobilize the organisms and the transfer device operates in coordination with the anesthetizing mechanism to automatically transfer immobilized organisms to the recipient container.

16. An apparatus for automatically transferring live organisms from a donor container to a recipient container, the apparatus comprising a gas manifold fluidly connectable to a gas source and configured to direct a flow of gas into the donor container such that the organisms are transferred by the flow of gas into the recipient container.

17. The apparatus of claim 16, wherein the gas manifold comprises an elongate gas-delivery tube configured such that, whenever the tube is inserted into the donor container and the gas source is activated to supply the flow of gas to the gas manifold, the tube directs the flow of gas from the donor container to the recipient container to blow the organisms from the donor container into the recipient container.

18. The apparatus of claim 16, further comprising a donor-container positioner and a recipient-container positioner for automatically positioning the donor container and the recipient container, respectively, at the gas manifold for transferring the organisms from the donor container to the recipient container.

19. An apparatus for automatically transferring live organisms from a donor container to a recipient container the apparatus comprising:

a plurality of donor containers, at least some of which contain live organisms;

a plurality of recipient containers for receiving organisms from respective donor containers;

at least one transfer device configured to transfer organisms from a donor container to a respective recipient container; and a robotic arm configured to automatically pick up a donor container and transfer the donor container to the transfer device and to pick up a recipient container and transfer the recipient container to the transfer device for transferring organisms from the donor container to the recipient container.

20. The apparatus of claim 19, further comprising a bar-code reader for reading bar codes on donor containers or recipient containers.

21. The apparatus of claim 20, wherein the robotic arm is configured to transfer donor containers or recipient containers to the bar-code reader for reading bar codes on said donor or recipient containers.

22. The apparatus of claim 19, further comprising a label maker for making labels and applying the labels to respective donor containers or recipient containers.

23. The apparatus of claim 22, wherein the robotic arm is configured to transfer donor containers or recipient containers to the label maker for receiving a label.

24. The apparatus of claim 19, wherein the donor containers are supported in a first container rack and the recipient containers are supported in a second container rack, each of the first and second container racks defining two rows of openings for receiving respective containers.

25. The apparatus of claim 24, wherein each of the first and second container racks has first and second side walls, with each side wall defining a plurality of windows to permit inspection of the donor and recipient containers through the side walls.

26. An apparatus for transferring organisms from a donor container to a recipient container, the apparatus comprising:

gas manifold fluidly connectable to a source of gas, the gas manifold being configured such that, whenever the donor container and the recipient container are positioned at the gas manifold and the source of gas is activated to supply gas to the gas manifold, a flow of gas is directed to blow the organisms from the donor container to the recipient container.

27. The apparatus of claim 26, further comprising a donor-container positioner for positioning the donor container at the gas manifold, and a recipient-container positioner for positioning the recipient container at the gas manifold.

28. The apparatus of claim 27, further comprising a robotic arm configured to automatically pick up the donor container and place the donor container in the donor-container positioner, and to pick up the recipient container and place the recipient container in the recipient-container positioner.

29. The apparatus of claim 26, further comprising an anesthetizing mechanism configured to automatically expose the organisms to an anesthetic before the organisms are transferred into the recipient container.

30. The apparatus of claim 29, wherein the anesthetizing mechanism is configured to inject an anesthetic gas into the donor container to immobilize the organisms before the insects are transferred into the recipient container.

31. An apparatus for transferring populations of organisms contained in donor containers to corresponding recipient containers, the apparatus comprising:

at least one transfer device configured to transfer a population of organisms from a donor container to a respective recipient container; and a robotic arm configured to automatically pick up a donor container and transfer said donor container to the transfer device and to pick up a corresponding recipient container and transfer said recipient container to the transfer device for transferring the organisms from said donor container to said recipient container.

32. The apparatus of claim 31, wherein the transfer device includes an anesthetic-delivery system for introducing an anesthetic into the donor containers, the anesthetic being effective to temporarily immobilize the organisms in the donor containers.

33. The apparatus of claim 31, wherein the transfer device includes a gas manifold fluidly connectable to a source of gas, wherein the gas manifold is configured such that, whenever a donor container and a recipient container are positioned at the gas manifold and the source of gas is activated to supply gas to the gas manifold, a flow of gas is directed to blow insects from said donor container to said recipient container.

34. The apparatus of claim 33, wherein the transfer device further comprises first and second container positioners, the first container positioner being configured to receive a donor container from the robotic arm and to position the donor container at the gas manifold, the second container positioner being configured to receive a recipient container from the robotic arm and to position the recipient container at the gas manifold.

35. The apparatus of claim 31, further comprising a bar-code reader for reading bar codes on donor containers or recipient containers.

36. The apparatus of claim 35, wherein the robotic arm is configured to automatically deliver donor containers or recipient containers to the bar-code reader for reading the bar codes on said donor or recipient container.

37. The apparatus of claim 31, further comprising a label maker for making labels and applying the labels to respective donor or recipient containers.

38. The apparatus of claim 37, wherein the robotic arm is configured to deliver donor containers or recipient containers to the label maker for receiving a label.

39. The apparatus of claims 31, wherein the robotic arm comprises a sensor for detecting the presence of a donor container or a recipient container at a selected location in three-dimensional space.

40. An apparatus for transferring organisms from a donor container to a recipient container, the apparatus comprising:

immobilizing means for temporarily immobilizing the organisms in the donor container; and transfer means for automatically transferring the organisms from the donor container to the recipient container, the transfer means being coordinated with the immobilizing means to automatically transfer the organisms after the organisms have been immobilized.

41. The apparatus of claim 40, wherein the means for temporarily immobilizing the organisms comprises an anesthetic-delivery system configured to deliver an anesthetic to the donor container to expose the organisms in the donor container to the anesthetic.

42. The apparatus of claim 40, wherein the means for transferring the organisms from the donor container to the recipient container comprises a gas manifold fluidly connectable to a source of gas and configured to direct a flow of gas into the donor container so as to blow the organisms from the donor container into the recipient container.

43. A method for transferring live organisms from a donor container to a recipient container, the method comprising:

temporarily immobilizing the organisms in the donor container by exposing the organisms to an anesthetic; and transferring the immobilized organisms from the donor container to the recipient container;

wherein the step of transferring the immobilized organisms comprises blowing the immobilized organisms from the donor container to the recipient container with a flow of a gas.

44. The method of claim 43, wherein the step of temporarily immobilizing the organisms comprises introducing an anesthetic gas into the donor container, the gas being effective to temporarily immobilize the organisms.

45. The method of claim 44, wherein the anesthetic gas comprises carbon dioxide gas.

46. The method of claim 43, wherein the organisms comprise adult insects, pupae, larvae, and eggs, and the step of blowing the immobilized organisms from the donor container to the recipient container with a flow of the gas comprises blowing the adult insects into the recipient container but not the pupae, larvae, and eggs.

47. The method of claim 43, wherein the organisms are flies.

48. A method for transferring live organisms from a donor container to a recipient container, the method comprising:

positioning the donor container and the recipient container such that an open top of the donor container is adjacent an open top of the recipient container; and directing a flow of gas into the donor container such that the organisms are carried by the flow of gas from the donor container to the recipient container.

49. The method of claim 48, further comprising immobilizing the organisms prior to transferring the organisms to the recipient container.

50. The method of claim 49, wherein the step of immobilizing the organisms comprises exposing the organisms to an anesthetic.

51. The method of claim 49, wherein the step of immobilizing the insects comprises inserting a needle into the donor container, the needle being fluidly connectable to a source of an anesthetic, and activating the source of the anesthetic so that the anesthetic is introduced into the donor container through the needle.

* * * * *